(12) United States Patent
Pereira et al.

(10) Patent No.: US 10,188,674 B2
(45) Date of Patent: Jan. 29, 2019

(54) PARENTERAL FORMULATIONS FOR ADMINISTERING MACROLIDE ANTIBIOTICS

(71) Applicant: Cempra Pharmaceuticals, Inc., Chapel Hill, NC (US)

(72) Inventors: David E. Pereira, Apex, NC (US); Sara Wu, Cary, NC (US); Prabhavathi Fernandes, Chapel Hill, NC (US)

(73) Assignee: CEMPRA PHARMACEUTICALS, INC., Chapel Hill, NC (US)

(*) Notice: Subject to any disclaimer, the term of this patent is extended or adjusted under 35 U.S.C. 154(b) by 0 days.

(21) Appl. No.: 14/387,643

(22) PCT Filed: Mar. 27, 2013

(86) PCT No.: PCT/US2013/034179
§ 371 (c)(1),
(2) Date: Sep. 24, 2014

(87) PCT Pub. No.: WO2013/148891
PCT Pub. Date: Oct. 3, 2013

(65) Prior Publication Data
US 2015/0342977 A1 Dec. 3, 2015

Related U.S. Application Data

(60) Provisional application No. 61/783,026, filed on Mar. 14, 2013, provisional application No. 61/616,196, filed on Mar. 27, 2012.

(51) Int. Cl.
| | | |
|---|---|---|
| A61K 47/12 | (2006.01) | |
| A61K 47/18 | (2017.01) | |
| A61K 31/7048 | (2006.01) | |
| A61K 47/22 | (2006.01) | |
| A61K 9/00 | (2006.01) | |

(52) U.S. Cl.
CPC ........ A61K 31/7048 (2013.01); A61K 9/0019 (2013.01); A61K 47/12 (2013.01); A61K 47/183 (2013.01); A61K 47/22 (2013.01)

(58) Field of Classification Search
CPC .. A61K 31/7048; A61K 9/0019; A61K 47/12; A61K 47/22; A61K 47/183
USPC .......................................................... 514/29
See application file for complete search history.

(56) References Cited

U.S. PATENT DOCUMENTS

| | | | |
|---|---|---|---|
| 1,354,753 A | 10/1920 | Howard | |
| 2,180,006 A | 11/1939 | Hasche | |
| 3,668,282 A | 6/1972 | Below | |
| 3,843,767 A | 10/1974 | Fabrizio | |
| 3,843,787 A | 10/1974 | Fabrizio | |
| 4,312,866 A * | 1/1982 | Caruso | C07D 233/64 514/183 |
| 4,331,803 A | 5/1982 | Watanabe | |
| 4,474,768 A | 10/1984 | Bright | |
| 4,716,153 A * | 12/1987 | Morishita | A61K 31/70 424/115 |
| 4,742,049 A | 5/1988 | Baker | |
| 4,886,792 A | 12/1989 | Djokic | |
| 4,990,602 A | 2/1991 | Morimoto | |
| 5,211,955 A | 5/1993 | Legros | |
| 5,444,051 A | 8/1995 | Agouridas | |
| 5,527,780 A | 6/1996 | Agouridas | |
| 5,543,400 A | 8/1996 | Agouridas | |
| 5,614,614 A | 3/1997 | Agouridas | |
| 5,633,006 A | 5/1997 | Catania et al. | |
| 5,635,485 A | 6/1997 | Agouridas | |
| 5,656,607 A | 8/1997 | Agouridas | |
| 5,747,467 A | 5/1998 | Agouridas | |
| 5,760,010 A | 6/1998 | Klein | |
| 5,760,233 A | 6/1998 | Agouridas | |
| 5,770,579 A | 6/1998 | Agouridas | |
| 5,834,428 A | 11/1998 | Drucker | |
| 5,985,844 A | 11/1999 | Heck | |
| 6,011,142 A | 1/2000 | Bonnet | |
| 6,020,521 A | 2/2000 | Randolph | |
| 6,028,181 A | 2/2000 | Or | |
| 6,096,714 A | 8/2000 | Agouridas | |
| 6,096,922 A | 8/2000 | Lai | |
| 6,121,432 A | 9/2000 | Bonnet | |
| 6,270,768 B1 | 8/2001 | OConnell | |
| 6,313,101 B1 | 11/2001 | Denis | |
| 6,395,300 B1 | 5/2002 | Liang | |
| 6,395,710 B1 | 5/2002 | Chu | |
| 6,407,074 B1 | 6/2002 | Bronk | |
| 6,407,257 B1 | 6/2002 | Agouridas et al. | |
| 6,420,535 B1 | 7/2002 | Phan | |
| 6,437,106 B1 | 8/2002 | Stoner | |
| 6,440,941 B1 | 8/2002 | Denis | |
| 6,455,505 B2 | 9/2002 | Agouridas | |
| 6,515,116 B2 | 2/2003 | Suh | |
| 6,555,524 B2 | 4/2003 | Kaneko | |
| 6,664,238 B1 | 12/2003 | Su | |
| 6,777,393 B2 | 8/2004 | Bronk | |
| 6,809,188 B1 | 10/2004 | Suh | |
| 6,849,608 B2 | 2/2005 | Su | |
| 6,890,907 B2 | 5/2005 | Speirs | |
| 7,056,893 B2 | 6/2006 | Roy | |
| 7,163,924 B2 | 1/2007 | Burger | |

(Continued)

FOREIGN PATENT DOCUMENTS

| | | |
|---|---|---|
| CN | 1343216 A | 4/2002 |
| CN | 1354753 | 6/2002 |

(Continued)

OTHER PUBLICATIONS

Wu, Amino Acids, 2009, 37, 1-17.*

(Continued)

*Primary Examiner* — Ganapathy Krishnan
(74) *Attorney, Agent, or Firm* — Brannon Sowers & Cracraft PC

(57) ABSTRACT

Pharmaceutical compositions adapted for the parenteral administration, including intravenous administration, of triazole containing macrolide antibiotics, and methods for their use in the treatment of bacterial, protozoal, and other infections are described herein.

28 Claims, 9 Drawing Sheets

(56) References Cited

U.S. PATENT DOCUMENTS

| | | | |
|---|---|---|---|
| 7,332,476 | B2 | 2/2008 | Burger |
| 7,375,234 | B2 | 5/2008 | Sharpless |
| 7,419,961 | B2 | 9/2008 | Napoletano |
| 7,601,695 | B2 * | 10/2009 | Liang .................. C07D 498/04 514/29 |
| 7,795,316 | B1 | 9/2010 | Kabra |
| 7,951,905 | B2 | 5/2011 | Schweizer |
| 8,012,943 | B2 | 9/2011 | Duffield |
| 8,247,394 | B2 | 8/2012 | Fernandes |
| 8,759,500 | B2 * | 6/2014 | Pereira .................. C07H 17/08 536/7.4 |
| 8,791,080 | B2 | 7/2014 | Fernandes |
| 8,796,232 | B2 * | 8/2014 | Fernandes ............. A61K 31/70 514/29 |
| 9,051,346 | B2 | 6/2015 | Pereira |
| 9,200,026 | B2 | 12/2015 | Liang |
| 2002/0009507 | A1 | 1/2002 | Weimer |
| 2002/0028781 | A1 | 3/2002 | Agouridas |
| 2002/0044967 | A1 | 4/2002 | Yamashita |
| 2002/0115621 | A1 | 8/2002 | Su |
| 2003/0143162 | A1 | 7/2003 | Speirs |
| 2003/0176327 | A1 | 9/2003 | Cassell |
| 2004/0009930 | A1 | 1/2004 | Su |
| 2004/0013737 | A1 | 1/2004 | Becourt |
| 2004/0014685 | A1 | 1/2004 | Mercep |
| 2005/0009764 | A1 | 1/2005 | Burger et al. |
| 2005/0014706 | A1 | 1/2005 | Falzari |
| 2005/0022242 | A1 | 1/2005 | Rosetti |
| 2005/0153905 | A1 | 7/2005 | Burger |
| 2005/0209172 | A1 | 9/2005 | Woo |
| 2005/0222427 | A1 | 10/2005 | Sharpless |
| 2006/0100164 | A1 | 5/2006 | Liang |
| 2006/0264385 | A1 | 11/2006 | Wang |
| 2007/0014857 | A1 | 1/2007 | Becourt |
| 2007/0015719 | A1 | 1/2007 | Jenkins |
| 2007/0082854 | A1 | 4/2007 | Deshpande |
| 2007/0167382 | A1 | 7/2007 | Finkelstein |
| 2007/0197518 | A1 | 8/2007 | Johnson |
| 2007/0281894 | A1 | 12/2007 | Gant |
| 2008/0001024 | A1 | 1/2008 | Bouchet |
| 2008/0113926 | A1 | 5/2008 | Ivezic |
| 2008/0132546 | A1 | 6/2008 | Basarab |
| 2008/0221048 | A1 | 9/2008 | Woo |
| 2008/0227730 | A1 | 9/2008 | Mutak |
| 2008/0241959 | A1 | 10/2008 | Culic |
| 2008/0287376 | A1 | 11/2008 | Das |
| 2009/0005325 | A1 | 1/2009 | Bas |
| 2009/0075916 | A1 | 3/2009 | Upadhyay |
| 2009/0076253 | A1 | 3/2009 | Kashimura |
| 2009/0087389 | A1 | 4/2009 | Leonard |
| 2009/0156517 | A1 | 6/2009 | Zhang |
| 2009/0209547 | A1 | 8/2009 | Kim |
| 2009/0209593 | A1 | 8/2009 | Liang |
| 2010/0028442 | A1 | 2/2010 | Archambeau |
| 2010/0143505 | A1 | 6/2010 | Gant |
| 2010/0216731 | A1 | 8/2010 | Pereira |
| 2011/0195920 | A1 | 8/2011 | Fernandes |
| 2012/0071429 | A1 | 3/2012 | Duffield |
| 2012/0122768 | A1 | 5/2012 | Onsoyen |
| 2012/0172323 | A1 | 7/2012 | Fernandes |
| 2012/0231995 | A1 | 9/2012 | Beck |
| 2013/0001034 | A1 | 1/2013 | Miyazaki |
| 2013/0011453 | A1 | 1/2013 | Latta |
| 2013/0018008 | A1 | 1/2013 | Pereira |
| 2013/0045937 | A1 | 2/2013 | Pereira |
| 2013/0053362 | A1 | 2/2013 | Castro |
| 2013/0066056 | A1 | 3/2013 | Pereira |
| 2013/0102523 | A1 | 4/2013 | Bartizal |
| 2013/0156705 | A1 | 6/2013 | Zhang |
| 2013/0164351 | A1 | 6/2013 | Fernandes |
| 2013/0172280 | A1 | 7/2013 | Pereira |
| 2013/0345410 | A1 | 12/2013 | Liang |
| 2014/0073770 | A1 | 3/2014 | Patil |
| 2014/0088062 | A1 | 3/2014 | Pereira |
| 2014/0148431 | A1 | 5/2014 | Patel |
| 2015/0342977 | A1 | 12/2015 | Pereira et al. |

FOREIGN PATENT DOCUMENTS

| | | | |
|---|---|---|---|
| CN | 101045063 | | 10/2007 |
| EP | 0248279 | A2 | 12/1987 |
| EP | 0680967 | A1 | 11/1995 |
| EP | 1024145 | A2 | 8/2000 |
| EP | 1167375 | | 1/2002 |
| GB | 891617 | | 3/1962 |
| GB | 891817 | * | 3/1962 |
| JP | S59175414 | | 10/1984 |
| JP | 06220082 | | 8/1994 |
| JP | H07126172 | | 5/1995 |
| JP | 08053489 | | 2/1996 |
| JP | 2000507573 | | 6/2000 |
| JP | 2000229993 | | 8/2000 |
| JP | 2000351794 | | 12/2000 |
| JP | 2002514197 | | 5/2002 |
| JP | 2004502736 | | 1/2004 |
| JP | 2006528667 | | 12/2006 |
| JP | 2007536371 | | 12/2007 |
| JP | 2008519788 | | 6/2008 |
| JP | 2008526948 | | 7/2008 |
| JP | 2008534504 | | 8/2008 |
| JP | 2009500356 | | 1/2009 |
| JP | 2009502788 | | 1/2009 |
| JP | 5914335 | | 5/2016 |
| RU | 2230748 | | 6/2004 |
| WO | 1997036912 | | 10/1997 |
| WO | 9830574 | A1 | 7/1998 |
| WO | 9856800 | A1 | 12/1998 |
| WO | 1998056801 | | 12/1998 |
| WO | 9921866 | A1 | 5/1999 |
| WO | 9928311 | A1 | 6/1999 |
| WO | 0012521 | A1 | 3/2000 |
| WO | 200031099 | A1 | 6/2000 |
| WO | 0044761 | A2 | 8/2000 |
| WO | 0062783 | A2 | 10/2000 |
| WO | 0110878 | A1 | 2/2001 |
| WO | 2001010787 | | 2/2001 |
| WO | 0250092 | A1 | 6/2002 |
| WO | 2002072111 | | 9/2002 |
| WO | 2003004509 | | 1/2003 |
| WO | 03072141 | A1 | 9/2003 |
| WO | 2004080391 | A2 | 9/2004 |
| WO | 2004101587 | | 11/2004 |
| WO | 2005074945 | | 8/2005 |
| WO | 05105821 | | 11/2005 |
| WO | 2005108412 | | 11/2005 |
| WO | 2006050941 | | 5/2006 |
| WO | 2006050942 | | 5/2006 |
| WO | 2006067589 | | 6/2006 |
| WO | 2006087642 | | 8/2006 |
| WO | 2006127987 | | 11/2006 |
| WO | 2007008537 | | 1/2007 |
| WO | 2007059307 | A2 | 5/2007 |
| WO | 2007060627 | | 5/2007 |
| WO | 20070143507 | | 12/2007 |
| WO | 2009053259 | | 4/2009 |
| WO | 2009055557 | A1 | 4/2009 |
| WO | 2010048599 | | 4/2010 |
| WO | 2010048600 | | 4/2010 |
| WO | 2010048601 | | 4/2010 |
| WO | 2011008193 | | 1/2011 |
| WO | 2011032052 | | 3/2011 |
| WO | 2011/112864 | | 9/2011 |
| WO | 2011112864 | A1 | 9/2011 |
| WO | 2011119604 | | 9/2011 |
| WO | WO 2011/112864 A1 * 9/2011 ............ A01N 43/02 |
| WO | 2011146829 | | 11/2011 |
| WO | 2012030513 | | 3/2012 |
| WO | 2012042534 | | 4/2012 |
| WO | 2013148891 | | 10/2013 |
| WO | 2014145210 | | 9/2014 |
| WO | 2014152326 | | 9/2014 |
| WO | 2014165792 | | 10/2014 |
| WO | 20150123256 | | 8/2015 |
| WO | 2015181723 | | 12/2015 |

(56) References Cited

FOREIGN PATENT DOCUMENTS

| WO | 2016022658 | 2/2016 |
| WO | 2016144833 | 9/2016 |
| WO | 2018045294 | 3/2018 |

OTHER PUBLICATIONS

PCT Search Report prepared for PCT/US13/34179, dated Jun. 28, 2013.
Putnam, S. D., Sader, H. S., Farrell, D. J., Biedenbach, D. J., & Castanheira, M. (2011). Antimicrobial characterisation of solithromycin (CEM-101), a novel fluoroketolide: activity against staphylococci and enterococci. International journal of antimicrobial agents, 37(1), 39-45.
Baker, William R., et al. "Modification of macrolide antibiotics. Synthesis of 11-deoxy-11-(carboxyamino)-6-O-methylerythromycin A 11, 12-(cyclic esters) via an intramolecular Michael reaction of O-carbamates with an. alpha.,.beta.-unsaturated ketone." The Journal of Organic Chemistry 53.10 (1988): 2340-2345.
Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.
Champney et al., 'Structure-Activity Relationships for Six Ketolide Antibiotics', Current Microbiology, 42:203-10 (2001).
Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).
Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).
LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.
Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, 1 Mar. 2005, pp. 1307-1310.
Or et al., 'Design, Synthesis, and Antimicrobial Activity of 6-0-Substituted Ketolides Active Against Resistant Respiratory Tract Pathogens', J. Med. Chem., 43:1045-49 (2000).
PCT Search Report and Written Opinion for PCT/US2011/037330 completed Aug. 26, 2011.
Phan, L.T. et al., 'Synthesis of 2-Fluoro-6-O-propargyl-11,12-carbamate Ketolides. A Novel Class of Antibiotics,' Org. Ltrs., 2:2951-2954 (2000).
Plata, Daniel J., et al. "The synthesis of ketolide antibiotic ABT-773 (cethromycin)." Tetrahedron 60.45 (2004): 10171-10180.
Romero et al., 'An efficient entry to new sugar modified ketolide antibiotics' Tetrahedron Letters, vol. 46, 2005, pp. 1483-1487.
Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).
Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 67:3057-64 (2002).
Vince, R., Almquist, R. G., Ritter, C. L., and Daluge, S., Antimicrobial Agents and Chemotherapy, vol. 8, No. 4, 1975, 439-443.
Zhenkun Ma & Peter A. Nemoto "Discovery and Development of Ketolides as a New Generation of MacrolideAntimicrobial Agents" Curr Med Chem—Anti-Infective Agents 1:15-34 (2002).
Bebear, C.M., et al., In vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).
Berge, Stephen M., et al., "Pharmaceutical Salts", 1977, Journal of Pharmaceutical Sciences, vol. 66, No. 1, pp. 1-19.
Bermudez, Luiz E., et al., "Telithromycin is Active Against Mycobacterium avium in Mice Despite Lacking Significant Activity in Standard In Vitro and Macrophage Assays and Is Associated with Low Frequency of Resistance During Treatment", 2001, Antimicrobal Agents and Chemotherapy, vol. 45, No. 8, pp. 2210-2214.
Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.
Cynamon, M. H., et al., "Activity of ABT-773 Against Mycobacterium avium Complex in the Beige Mouse Model", 2000, Antimicrobal Agents and Chemotherapy, vol. 44, No. 10, pp. 2895-2896.
Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.
Holzer, G., et al., "Ka1,2 and KB1,3 X-Ray Emission Lines of the 3d Transition Metals", Dec. 1997, Physical Review, vol. 56, No. 6, pp. 4554-4568.
Inglesby, Thomas V., et al., "Anthrax as a Biological Weapon, 2002", 2002, Journal of the American Medical Association, vol. 287, No. 17, pp. 2236-2252.
Laine, Loren, et al., "Prospective comparison of H&E, Giemsa and Genta stains for the diagnosis of Helicobacter pylori," 1997, Gastrointestinal Endoscopy, vol. 45, No. 6, pp. 463-467.
Lee, Adrian et al., "A standard mouse model of Helicobacter pylori infection: introducing the Sydney Strain," 1997, Gastroenterology, vol. 112, pp. 1386-1397.
Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.
Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.
Patel, Ramesh N., "Stereoselective Biocatalysis", 2000, Bristol-Myers Squibb Research Institute; pp. 775-797.
Barcia-Macay, Maritza, et al., 'Pharmacodynamic Evaluation of the Intracellular Activities of Antibiotics Against Staphylococcus aureus in a Model of THP-1 Macrophages', 2006, Antimicrobial Agents and Chemotherapy. vol. 50, No. 3, pp. 841-851.
Bermudez, Luiz E., et al., "EDP-420, a Bicyclolide (Bridged Bicyclic Macrolide), Is Active Against Mcyobacterium avium", 2007, Antimicrobal Agents and Chemotherapy, vol. 51, No. 5, pp. 1666-1670.
Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799, 800.
Drusano, G. L., et al., "Is 60 Days of Ciprofloxacin Adminstration Necessary for Postexposure Prophylaxis for Bacillus Anthracis?", 2008, Antimicrobial Agents and Chemotherapy. vol. 52, No. 11, pp. 3973-3979.
Duffy, L., et al., Fluoroquinolone resistance in Ureaplasma parvum in the United States, J Clin Microbiol 44:1590-1591 (2006).
Jensen, J.S., et al., Azithromycin Treatment Failure in Mycoplasma genitaliumPositive Patients with Nongonococcal Urethritis Is Associated with Induced Macrolide Resistance, Clin Infect Dis 47:1546-53 (2008).
Lemaire, Sandrine, et al., "Cellular Accumulation and Pharmacodynamic Evaluation of the Intracellular Activity of CEM-101, a Novel Fluoroketolide, Against Staphylococcus aureus, Listeria Monocytogenes and Legionella Pneumophila in Human THP-1 Macrophages", 2009, Antimicrobial Agents and Chemotherapy. vol. 53, No. 9, pp. 3734-3743.
Li, X., et al., Emerging macrolide resistance in Mycoplasma pneumoniae in children: detection and characterization of resistant isolates, Pediatr Infect Dis J, 28:693-696 (2009).
Physicians' Desk Reference, p. 2905, (2007).
Vennerstrom, Jonathan L., et al., "Identification of an Antimalarial Synthetic Trioxolane Drug Development Candidate", 2004, Letters to Nature, vol. 430, pp. 900-904.

(56) References Cited

OTHER PUBLICATIONS

Waites, K.B., et al., Mycoplasmas and ureaplasmas as neonatal pathogens, Clin Microbiol Rev 18:757-89 (2005).

Zuckerman, "Macrolides and ketolides: azithromycin, clarithromycin, telithromycin", Infectious Disease Clinics of North America, vol. 18, (2004), pp. 621-649.

Jones et al.: 'MIC Quality Control Guidelines and Disk Diffusion Test Optimization for CEM-101, a Novel Fluoroketolide' Journal of Clinical Microbiology vol. 48, No. 4, Dec. 30, 2009, pp. 1470-1473.

PCT International Search Report and Written Opinion for PCT/US2011/029424, dated May 25, 2011.

Feder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.

Caira MR, "Crystalline polymorphism of orgainic compounds," Design of Organic Solids, Topics in Current Chemistry, Springer Berlin Heidelberg, 1998, p. 163-208.

Pathak et al., "Enzymatic Protecting Group Techniques in Organic Synthesis," Stereosel, Biocatal., 2000; pp. 775-797.

Katz, Leonard, and Gary W. Ashley. "Translation and protein synthesis: macrolides." Chemical reviews 105.2 (2005): 499-528.

Threlfall, Terence L. "Analysis of organic polymorphs. A review." Analyst 120.10 (1995): 2435-2460.

Petit, Samuel, and Gérard Coquerel. "The amorphous state." Polymorphism: In the Pharmaceutical Industry 10 (2006): 1.

Organic Compounds Crystal Manufacture Handbook—Principles and Knowhow, 2008, pp. 57 to 84.

Hancock, Bruno C., Sheri L. Shamblin, and George Zografi. "Molecular mobility of amorphous pharmaceutical solids below their glass transition temperatures." Pharmaceutical research 12.6 (1995): 799-806.

Ashizawa, Kazuhide, "Physico-Chemical Studies on the molecular Details of Drug Crystals," Phar Tech Japan, 2002, vol. 18, No. 10. pp. 81-96.

PCT Search Report and Written Opinion prepared for PCT/US2009/061978 dated Dec. 9, 2009.

European Search Report for EP 09 82 2827, dated Mar. 21, 2012.

International Search Report for PCT/US2009/061977, dated Dec. 23, 2009, (3 pages).

PCT Search Report/Written Opinion prepared for PCT/US2010/048540, dated Oct. 21, 2010.

Byrn, S., Pfeiffer, R., Ganey, M., Hoiberg, C., & Poochikian, G. (1995). Pharmaceutical solids: a strategic approach to regulatory considerations. Pharmaceutical research, 12(7), 945-954.

Sumerkan, B., Aygen, B., Doganay, M., & Sehmen, E. (1996). Antimicrobial susceptibility of Bacillus anthracis against macrolides. Salisbury Med Bull Supplement, 87, 138.

Maurin, M., Mersali, N. F., & Raoult, D. (2000). Bactericidal activities of antibiotics against intracellular Francisella tularensis. Antimicrobial agents and chemotherapy, 44(12), 3428-3431.

Luna, V. A., King, D. S., Gulledge, J., Cannons, A. C., Amuso, P. T., & Cattani, J. (2007). Susceptibility of Bacillus anthracis, Bacillus cereus, Bacillus mycoides, Bacillus pseudomycoides and Bacillus thuringiensis to 24 antimicrobials using Sensititre® automated microbroth dilution and Etest® agar gradient diffusion methods. Journal of antimicrobial chemotherapy, 60(3), 555-567.

Barthel, D., Schlitzer, M., & Pradel, G. (2008). Telithromycin and quinupristin-dalfopristin induce delayed death in Plasmodium falciparum. Antimicrobial agents and chemotherapy, 52(2), 774-777.

Still, J. G., et al. "Single Oral Dose Pharmacokinetics and Safety of CEM-101 in Healthy Subjects." 46th Annual Meeting. Idsa, 2008.

Lee, Joo Hyun, and Myung Gull Lee. "Dose-dependent pharmacokinetics of telithromycin after intravenous and oral administration to rats: contribution of intestinal first-pass effect to low bioavailability." J. Pharm. Pharm. Sci 10 (2007): 37-50.

Chen, M., Muri, E. M., Jacob, T. M., & Williamson, J. S. (2003). Synthesis and bioactivity of erythromycin derivatives. Medicinal chemistry research, 12(3), 111-129.

Kerdesky, F. A., Premchandran, R., Wayne, G. S., Chang, S. J., Pease, J. P., Bhagavatula, L., . . . & King, S. A. (2002). Synthesis of 2'-O-Benzoyl-3-keto-6-O-propargyl-11, 12-carbamoyl Erythromycin A. Organic process research & development, 6(6), 869-875.

Zhu, Z. J., Krasnykh, O., Pan, D., Petukhova, V., Yu, G., Liu, Y., . . . & Franzblau, S. G. (2008). Structure-activity relationships of macrolides against *Mycobacterium tuberculosis*. Tuberculosis, 88, S49-S63.

International Search Report Written Opinion for PCT/US2008/080936 completed Dec. 8, 2008.

Putnam S. D. et al, Antimicrobial Characterization of Solithromycin (CEM-101), A Novel Fluroroketolide: Activity Against Staphlococci and Enterococci. International Journal of Antimicrobial Agents, vol. 37, No. 1, 2011, pp. 39-45.

Written Opinion, Singapore Application No. 11201405895U: Intellectual Property Office of Singapore; dated Mar. 31, 2015, 6 pages.

Database WPI Week 200822 Thomson Scientific, London, GB; AN 2008-D02982.

Zimmermann, Torsten, et al. "Comparative tolerability of intravenous azithromycin, clarithromycin and erythromycin in healthy volunteers." Clinical Drug Investigation 21.8 (2001): 527-536.

Luke, D. R., and G. Foulds. "Toleration of intravenous azithromycin." The Annals of pharmacotherapy 31.9 (1997): abstract only.

Cannon, John B., N. Adeyinka Williams, and Karen J. Papp. "Reduction of pain on intravenous infusion with bile salt formulations for a macrolide antibiotic." International journal of pharmaceutics 114.1 (1995): abstract only.

Lu, Yan, YanJiao Wang, and Xing Tang. "Formulation and thermal sterile stability of a less painful intravenous clarithromycin emulsion containing vitamin E." International journal of pharmaceutics 346.1 (2008): abstract only.

Llano-Sotelo, B., D. Klepacki, and A. S. Mankin. 2008. Binding and action of CEM-10, a new macrolide/ketolide in development for treating infections with macrolide-resistant and macrolide-susceptible bacteria. 48th Annu. Intersci. Conf. Antimicrob. Agents Chemother./46th Infect. Dis. Soc. Am. Ann. Meet., abstr. F1-3983.

International Search Report for PCT/US2015/015353, dated May 14, 2015, (8 pages).

Ferris, C. F., Lu, S. F., Messenger, T., Guilion, C. D., Heindel, N., Miller, M., . . . & Simon, N. G. (2006). Orally active vasopressin V1a receptor antagonist, SRX251, selectively blocks aggressive behavior. Pharmacology Biochemistry and Behavior, 83(2), 169-174.

Amsden, G. W. "Anti-inflammatory effects of macrolides"—"an underappreciated benefit in the treatment of community-acquired respiratory tract infections and chronic inflammatory pulmonary conditions?." Journal of Antimicrobial Chemotherapy 55.1 (2005): 10-21.

De Jong, J. T., et al. "[Large-scale, acute, bacterial gastroenteritis caused by the enterotoxin of *Staphylococcus aureus* after a barbecue]." Nederlands tijdschrift voor geneeskunde 148.43 (2004): 2136-2140.

Raj, Pushker. "Pathogenesis and laboratory diagnosis of *Escherichia coli*"—"associated enteritis." Clinical microbiology Newsletter 15.12 (1993): 89-93.

Ikeue, T., et al. "[Pneumonia caused by Nocardia nova]." Nihon Kokyuki Gakkai zasshi=the journal of the Japanese Respiratory Society 39.7 (2001): 492-497.

Thakkar, Shyam, and Radheshyam Agrawal. "A case of *Staphylococcus aureus* enterocolitis: a rare entity," Gastroenterology & hepatology 6.2 (2010): 115-117.

Wain, Harry, and Paul A. Blackstone. "Staphylococcal Gastroenteritis." The American journal of digestive diseases 1.10 (1956): 424.

Boyce, Thomas G., "Staphylococcal Food Poisoning," Merck Manuals (2015) 2 pages.

Lv Yang et al., "Polymorphic Drugs." Oct. 31, 2009, pp. 110-111.

Le Loir, Yves, Florence Baron, and Michel Gautier. "*Staphylococcus aureus* and food poisoning." Genet Mol Res 2.1 (2003): 63-76.

Brittain HG editor "Polymorphism in pharmaceutical solids", Chapter 1, p. 1-10 (Grant DJW) and Chapter 5, p. 183-226 (1999).

(56) References Cited

OTHER PUBLICATIONS

Graeme, A. O'May, Nigel Reynolds, and George T. Macfarlane. "Effect of pH on an in vitro model of gastric microbiota in enteral nutrition patients." Applied and environmental microbiology 71.8 (2005): 4777-4783.

Cotter, Paul D., and Colin Hill. "Surviving the acid test: responses of gram-positive bacteria to low pH." Microbiology and Molecular Biology Reviews 67.3 (2003): 429-453.

Wain, Harry, and Paul A. Blackstone. "Staphylococcal Gastroenteritis." The American journal of digestive diseases 1.10 (1956): 424-429.

Lyczak, J. B., Cannon, C. L., & Pier, G. B. (2002). Lung infections associated with cystic fibrosis. Clinical microbiology reviews, 15(2), 194-222.

Denis, Alexis, et al. "Synthesis and antibacterial activity of HMR 3647 a new ketolide highly potent against erythromycin-resistant and susceptible pathogens." Bioorganic & medicinal chemistry letters 9.21 (1999): 3075-3080.

Bryskier, A. "Ketolides""telithromycin, an example of a new class of antibacterial agents." Clinical Microbiology and Infection 6.12 (2000): 661-669.

Morimoto, Shigeo, et al. "Chemical modification of erythromycins. I. Synthesis and antibacterial activity of 6-O-methylerythromycins A." The Journal of antibiotics 37.2 (1984): 187-189.

Hällgren, Anita, et al. "Antimicrobial susceptibility patterns of enterococci in intensive care units in Sweden evaluated by different MIC breakpoint systems." Journal of Antimicrobial Chemotherapy 48.1 (2001): 53-62.

Fernandes, P., et al. Intravenous Formulation of Solithromycin, a Painless Macrolide Antibiotic in a Rabbit Intravenous Injection Model, 2011, 5 pages.

Allen Loyd V Jr, Acidifying Agents, Featured Excipient. International Journal of Pharmaceutical Compounding, Dec. 31, 1999, vol. 3, No. 4, pp. 309 (abstract only).

Yatin R. G. et al., Excipients for Protein Drugs. Excipient Development for Pharmaceutical, Biotechnology, and Drug Delivery Systems, Jul. 28, 2006, pp. 299-300.

Fernandes, P., et al. "Solithromycin Macrolide Antibiotic." Drugs of the Future 36.10 (2011): 751-758.

Raoul, Jennifer M., Marc R. Peterson, and Theresa C. Peterson. "A novel drug interaction between the quinolone antibiotic ciprofloxacin and a chiral metabolite of pentoxifylline." Biochemical pharmacology 74.4 (2007): 639-646.

Salzer, W. (2005). Antimicrobial-resistant gram-positive bacteria in PD peritonitis and the newer antibiotics used to treat them. Peritoneal Dialysis International, 25(4), 313-319.

Caplus abstract of WO 01/10878, Accession No. 2001 :115160 (2001 ).

"FDA Briefing Document Solithromycin Oral Capsule and Injection Meeting of the Antimicrobial Drugs Advisory Committee (AMDAC)", Nov. 4, 2016, 36, pages.

"Guidance for Industry Community-Acquired Bacterial Pneumonia: Developing Drugs for Treatment", U.S. Dept of Health and Human Services, FDA, Center for Drug Evaluation and Research, Jan. 2014, 37 pages.

Fernandes, P., Hashiguchi, T., Fujii, M., & Yoneyama, H. (2014). Anti-NASH effects of solithromycin in NASH-HCC mouse model. Gastroenterology, 146(suppl 1), S145-6.

Lee, Joo H., and Myung G. Lee. "Telithromycin pharmacokinetics in rat model of diabetes mellitus induced by alloxan or streptozotocin." Pharmaceutical research 25.8 (2008): 1915-1924.

Bosnar, Martina, et al. "N'-substituted-2'-O, 3'-N-carbonimidoyl bridged macrolides: novel anti-inflammatory macrolides without antimicrobial activity." Journal of medicinal chemistry 55.13 (2012): 6111-6123.

Glassford, Ian, et et al. "Ribosome-templated azide-alkyne cycloadditions: synthesis of potent macrolide antibiotics by in situ click chemistry." Journal of the American Chemical Society 138.9 (2016): 3136-3144.

Carboni, Bertrand, Aziza Benalil, and Michel Vaultier. "Aliphatic amino azides as key building blocks for efficient polyamine syntheses." The Journal of Organic Chemistry 5814 (1993): 3736-3741.

Wu, G. (2009). Amino acids: metabolism, functions, and nutrition. Amino acids, 37(1), 1-17.

Yajima, Toshio, et al. "Method of evaluation of the bitterness of clarithromycin dry syrup." Chemical and pharmaceutical bulletin 50.2 (2002): 147-152.

Denis, F., et al. "Microbiologic efficacy of 3-day treatment with azithromycin 1.5% eyedrops for purulent bacterial conjunctivitis." European journal of ophthalmology 18.6 (2008): 858-868.

"8.9—Flash Column Chromatography Guide." 5.301 Chemistry Laboratory Techniques, January IAP 2012, 6 pages.

Bučar, D. K., Lancaster, R. W., & Bernstein, J. (2015). Disappearing polymorphs revisited. Angewandte Chemie International Edition, 54(24), 6972-6993.

Certified copy of priority document U.S. Appl. No. 61/312,417, filed Mar. 10, 2010, 26 pages.

Certified copy of priority document U.S. Appl. No. 61/316,063, filed Mar. 22, 2010, 36 pages.

Decision rejection the opposition for EP Application No. 117600684, dated May 17, 2018, 24, apges.

\* cited by examiner

PARENTERAL FORMULATIONS FOR ADMINISTERING MACROLIDE ANTIBIOTICS

CROSS-REFERENCE TO RELATED APPLICATION

This application is a U.S. national application under 37 C.F.R. § 371(b) of International Application Serial No. PCT/US2013/034179 filed Mar. 27, 2013, which claims the benefit under 35 U.S.C. § 119(e) of U.S. Provisional Application Ser. No. 61/616,196, filed Mar. 27, 2012 and U.S. Provisional Application Ser. No. 61/783,026, filed Mar. 14, 2013, the entire disclosures of which are incorporated herein by reference.

TECHNICAL FIELD

The invention described herein pertains to pharmaceutical compositions adapted for the parenteral administration, including intravenous administration, of triazole containing macrolide antibiotics, and methods for their use in the treatment of bacterial, protozoal, and other infections. In particular, the invention described herein pertains to pharmaceutical compositions adapted for the parenteral administration, including intravenous administration of the ketolide antibiotics, such as CEM-101, also known as solithromycin, and related compounds, and methods for their use in the treatment of bacterial, protozoal, and other infections.

BACKGROUND AND SUMMARY OF THE INVENTION

Macrolide antibiotics, characterized by a large lactone ring to which are attached one or more deoxy sugars, usually cladinose and desosamine, are antimicrobial drugs that are active against aerobic and anaerobic gram positive cocci and are prescribed for the treatment of a number of infections, including respiratory tract and soft tissue infections. The macrolides, which belong to the polyketide class of natural products, function by reversibly binding to the 50S subunit of the bacterial ribosome, blocking protein synthesis and preventing bacterial growth and reproduction. Although this action is primarily bacteriostatic, certain triazole-containing fluoroketolide macrolides are bactericidal. Other macrolides may be bactericidal at higher concentrations.

Ketolides, which are semi-synthetic derivatives of the 14-membered macrolide erythromycin A, belong to the class of drugs used to treat respiratory tract infections. These drugs are effective against macrolide-resistant bacteria because of their ability to bind to two sites on the bacterial ribosome. Even so, acquired bacterial resistance to macrolides may occur, such as by post-transcriptional methylation of the 23S bacterial ribosome. This resistance results in cross-resistance to macrolides, lincosamides and streptogramins. Although rare, acquired resistance also can result from the production of drug-inactivating enzymes such as esterases or kinases, as well as the production of active ATP-dependent efflux proteins that transport macrolides out of the cell. A significant fraction of pneumococci are resistant to currently available antibiotics.

Erythromycin and the semi-synthetic derivatives azithromycin and clarithromycin are among the currently approved macrolide antibiotics. Telithromycin and cethromycin belong to the ketolide group of antibiotics. Oral administration has been accomplished for many macrolides and ketolides, including erythromycin, clarithromycin, telithromycin, and azithromycin. Erythromycin is also formulated as a lactobionate salt for injection; azithromycin is also formulated as a citrate salt for injection; and clarithromycin is available in some countries formulated as a lactobionate salt for injection. Ketolides, such as telithromycin and cethromycin have not been approved for parenteral administration, including IV administration. Unlike the oral counterparts, the corresponding parenteral administration, such as intravenous (IV) and intramuscular (IM) administration of known macrolides and ketolides, especially approved macrolides such as erythromycin, clarithromycin, telithromycin, and azithromycin, has been hampered by pharmacologic pain upon administration, and adverse side effects that may arise from the substantially different pharmacokinetics and pharmacodynamics accompanying parenteral administration compared to oral administration. For example, erythromycin, clarithromycin, and azithromycin have been reported to be painful when administered parenterally, leading to limitations on their use, issues with patient compliance, and other disadvantages.

Currently, there are no ketolides approved for parenteral administration, including intravenous administration. Accordingly, a need exists for alternative parenteral formulations, and methods for using such parenteral formulations, of ketolides in the treatment of bacterial, protozoal, and other infections. In addition, a need exists for parenteral formulations, and methods for using such parenteral formulations, of ketolides that may be administered at higher concentrations, and at faster rates.

It has been unexpectedly discovered that conventional formulations, such as formulations that include lactobionate salts, citrate salts, and/or physioloigcal saline, are not readily adaptable for use with triazole-containing ketolide antibiotics. Such conventional formulations require undue optimization to provide compositions and methods for treating bacterial, protozoal, and other infections without excessive pain, or other adverse side effects. In particular, such conventional formulations may not be administered in high concentrations, or at rapid rates due to pain, or other adverse side effects.

It has also been unexpectedly discovered that formulations of triazole-containing ketolide antibiotics that include one or more lactic acids, one or more amino acids, or combinations thereof, including any pharmaceutically acceptable salts of the foregoing, are useful for the parenteral delivery of such triazole-containing ketolide antibiotics.

Illustrative triazole-containing ketolide antibiotics include compounds described in WO 2004/080391, and related compounds. Further illustrative triazole-containing ketolide antibiotics include compounds of the formula:

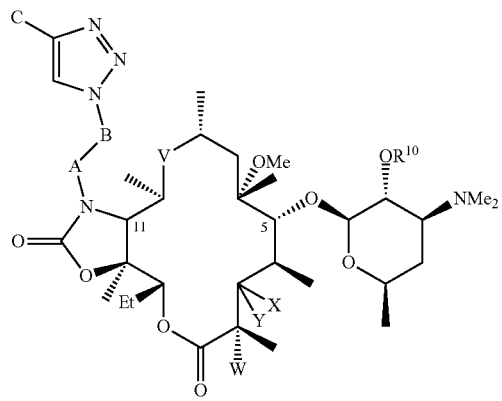

and pharmaceutically acceptable salts, solvates, and hydrates thereof, wherein:

$R^{10}$ is hydrogen, acyl or a prodrug moiety;

X and Y are taken together with the attached carbon to form carbonyl;

V is C(O);

W is H, F, Cl, Br, I, or OH;

A is $CH_2$, C(O), C(O)O, C(O)NH, $S(O)_2$, $S(O)_2NH$, or $C(O)NHS(O)_2$;

B is C2-C10 alkenylene, or C1-C10 alkylene, such as $(CH_2)_n$ where n is an integer ranging from 1-10, from 2-6, or from 3-5; and C is hydrogen, hydroxy, acyl, acyloxy, sulfonyl, ureido, or carbamoyl, or alkyl, alkoxy, heteroalkyl, heteroalkoxy, aryl, arylalkyl, heteroaryl, or heteroarylalkyl, each of which is optionally substituted.

Further illustrative triazole-containing ketolide antibiotics include the fluoroketolide compound solithromycin (SOL), Chemical Abstracts Registry Number 760981-83-7, and having the following structure:

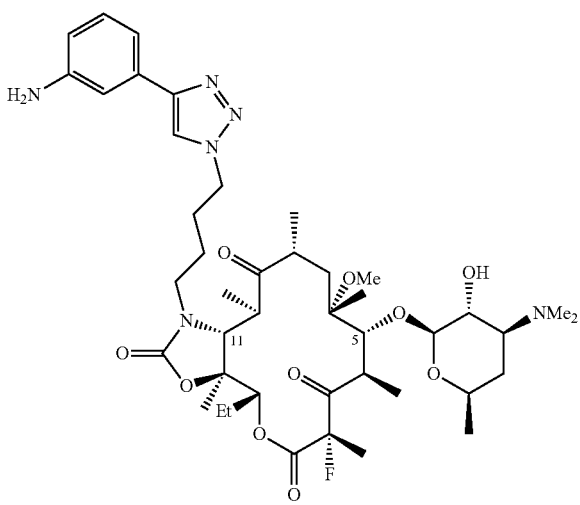 [SMILES: CC[C@H]1OC(=O)[C@@](C)(F)C(=O)[C@H](C)[C@@H](O[C@@H]2O[C@H](C)C[C@H](N(C)C)[C@H]2O)[C@@](C)(OC)C[C@@H](C)C(=O)[C@H](C)[C@H]2N(CCCCn3cc(-c4cccc(N)c4)nn3)C(=O)O[C@]12C]

and pharmaceutically acceptable salts, hydrates, solvates, esters, and prodrugs thereof. SOL is also described in international patent application, publication number WO 2004/080391. Solithromycin is also known as CEM-101 and as OP-1068. The preparation of SOL and related compounds is described in WO 2009/055557. The disclosure of each of the foregoing publications, and each additional publication cited herein are incorporated herein by reference.

Also described herein are solid, solution, and liquid formulations for such other therapeutic compounds that are characterized by low solubility and/or low basicity. It has been surprisingly discovered that the formulations described herein that include of one or more lactic acids, one or more amino acids, or combinations thereof, including any pharmaceutically acceptable salts of the foregoing, are useful for the parenteral delivery of such low solubility and/or low basicity therapeutic compounds.

Without being bound by theory, it is believed herein that the formulations described herein improve the solubility of such therapeutic compounds, including such therapeutic compounds that are weakly basic. In another embodiment, described herein are pharmaceutical compositions comprising lactic acid and pharmaceutically acceptable salts thereof adapted for the parenteral administration of low solubility and/or low basicity therapeutic compounds. In another embodiment, described herein are pharmaceutical compositions comprising amino acid and pharmaceutically acceptable salts thereof adapted for the parenteral administration of low solubility and/or low basicity therapeutic compounds. In another embodiment, described herein are pharmaceutical compositions comprising lactic acid and amino acids, and pharmaceutically acceptable salts thereof, adapted for the parenteral administration of low solubility and/or low basicity therapeutic compounds. The solid, liquid, and solution formulations described herein solve the problems of administering low solubility and/or weakly basic therapeutic compounds, such as triazole-containing macrolide antibiotics.

DETAILED DESCRIPTION

Figure 1:
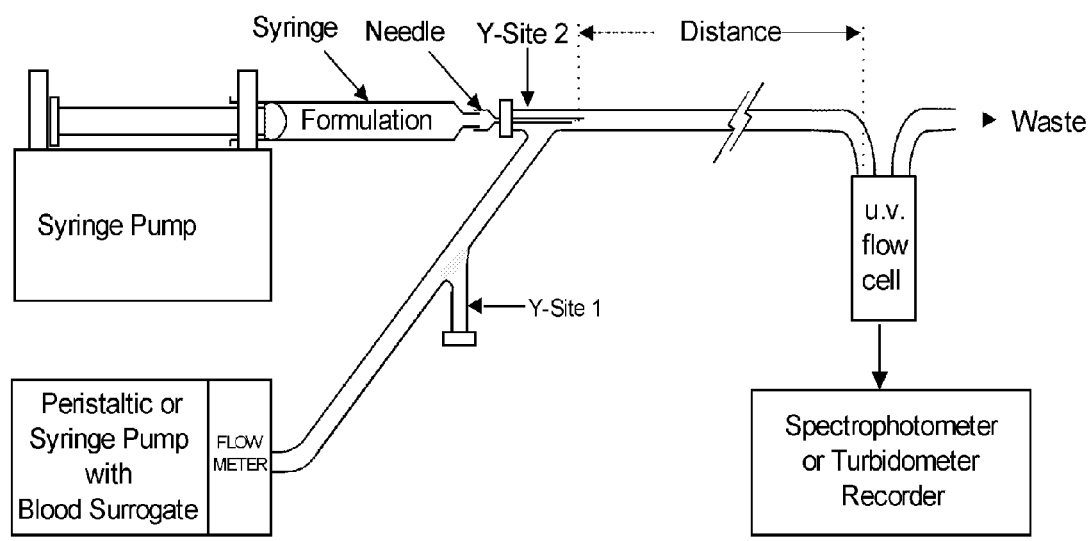
FIG. 1 shows a diagram of the dynamic in vitro apparatus for evaluating precipitation upon injection of an infusion solution.
Figure 2:
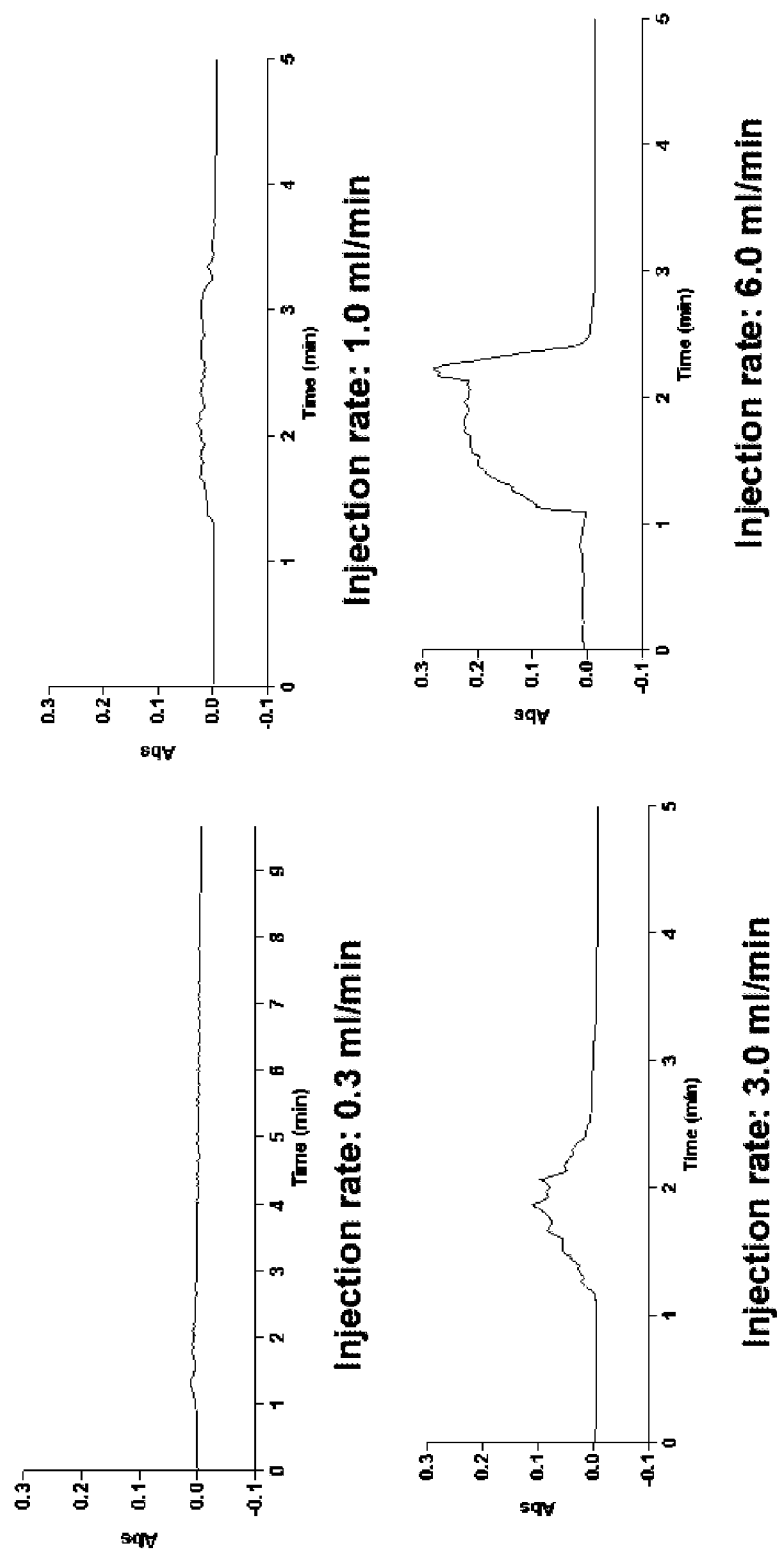
FIG. 2 shows the traces in the dynamic precipitation model for the CEM-101/Mannitol/Tartrate Formulation at 3 mg/mL in 0.45% Saline, infused at the injection rate of 0.3, 1.0, 3.0 and 6.0 mL/min (infusions started at t=1.0 min).
Figure 3:
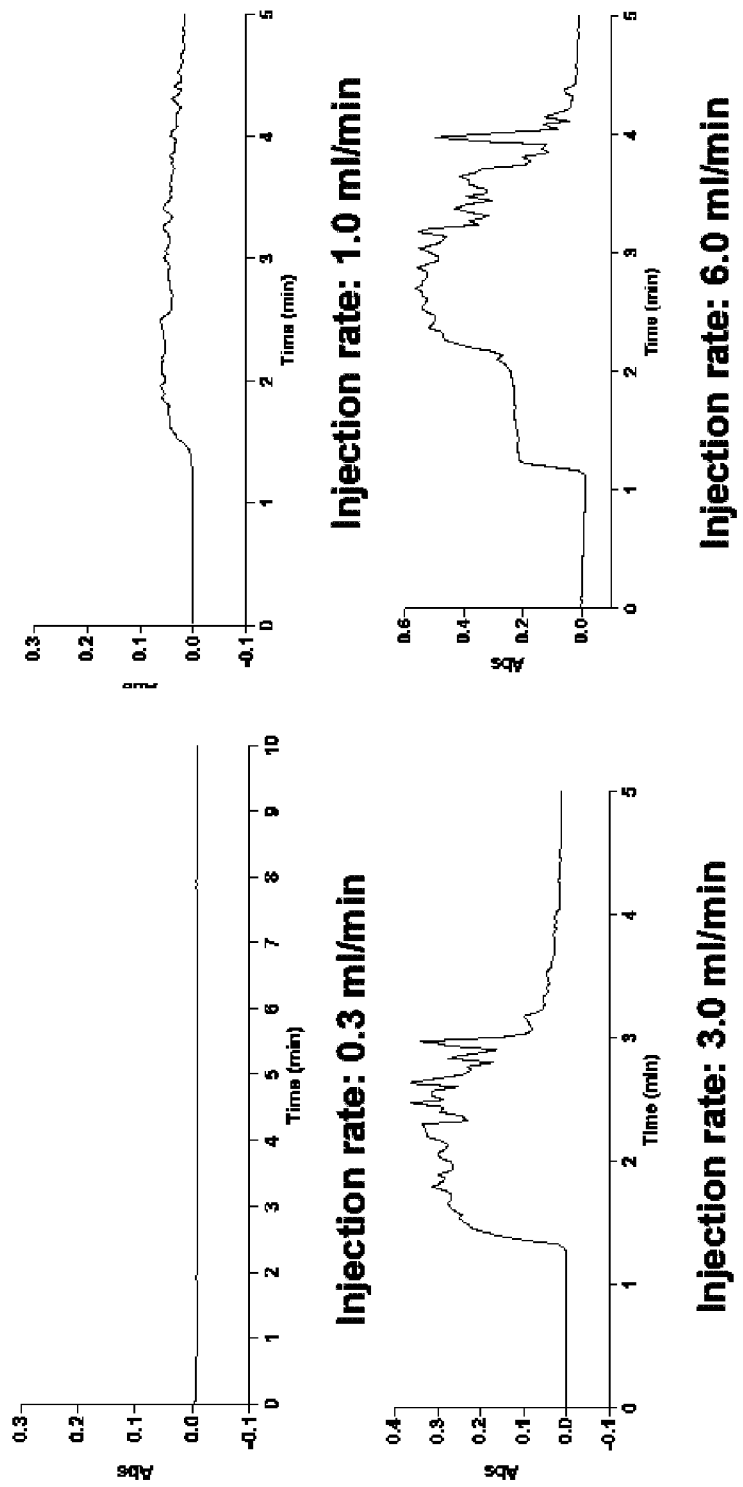
FIG. 3 shows the traces in the dynamic precipitation model for the CEM-101/Mannitol/Tartrate Formulation at 3 mg/mL in 5% Mannitol, infused at the injection rate of 0.3, 1.0, 3.0 and 6.0 mL/min (infusions started at t=1.0 min).
Figure 4:
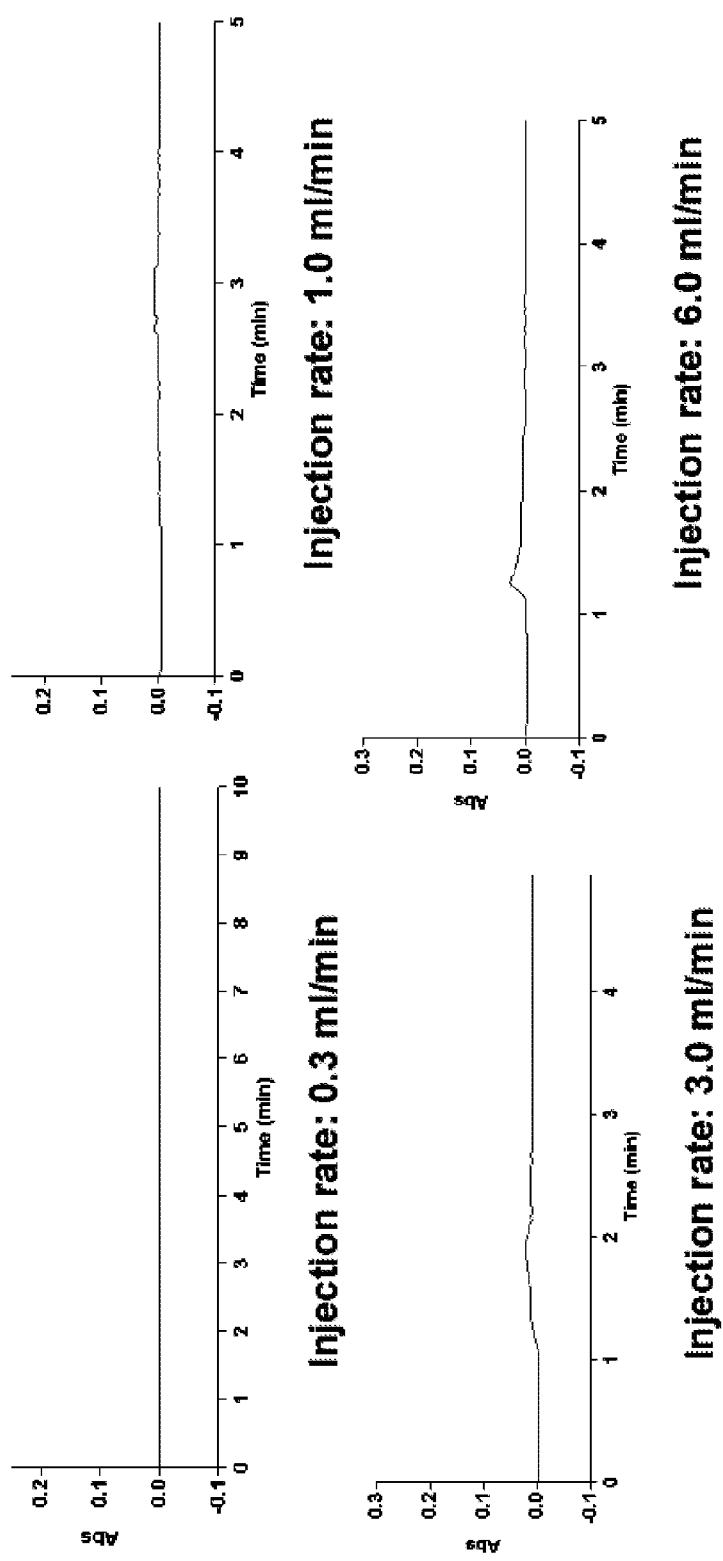
FIG. 4 shows the traces in the dynamic precipitation model for the CEM-101/Mannitol/Tartrate Formulation at 1 mg/mL in 5% Mannitol, infused at the injection rate of 0.3, 1.0, 3.0 and 6.0 mL/min (infusions started at t=1.0 min).
Figure 5:
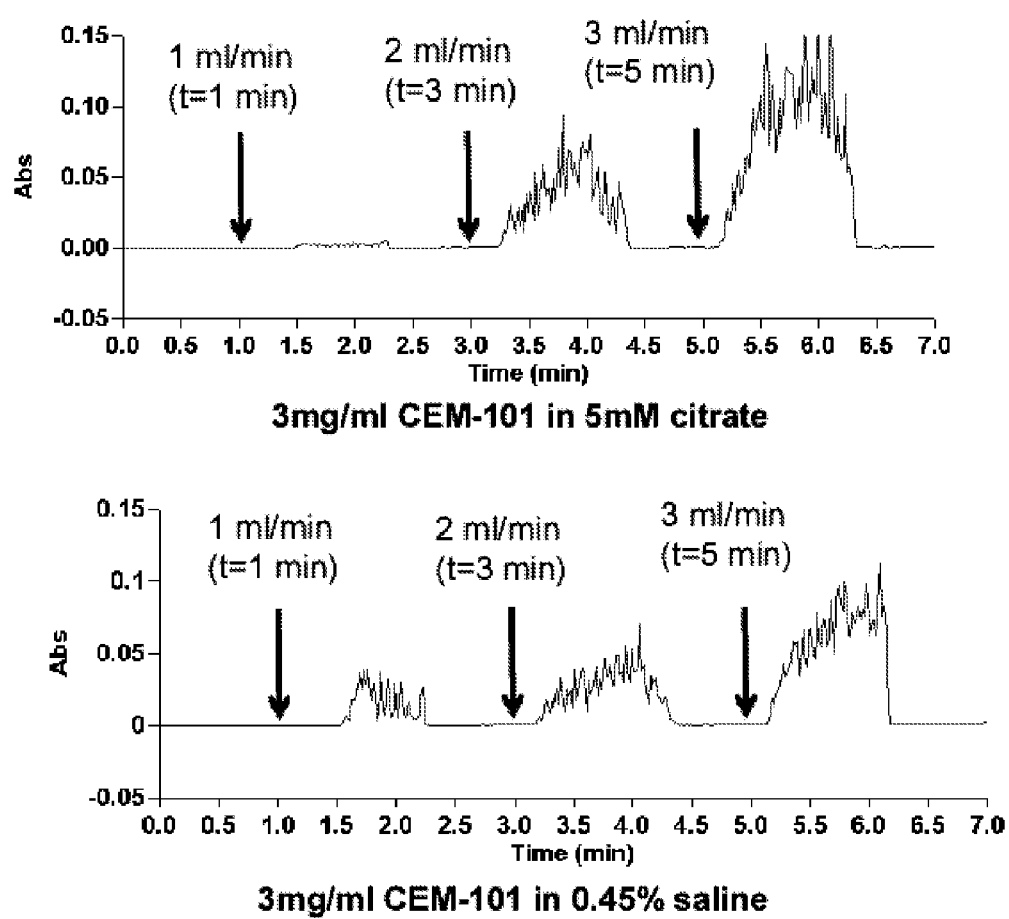
FIG. 5 the traces in the dynamic precipitation model for the comparison of the 3 mg/mL CEM-101/Mannitol/Tartrate Formulation (CEM-101) in 5 mM citrate buffer at pH 4 with the 3 mg/mL CEM-101/Mannitol/Tartrate Formulation (CEM-101) in 0.45% saline at infusion rates of 1 mL/min (t=1 min), 2 mL/min (t=3 min) and 3 mL/min (t=5 min).
Figure 6A:
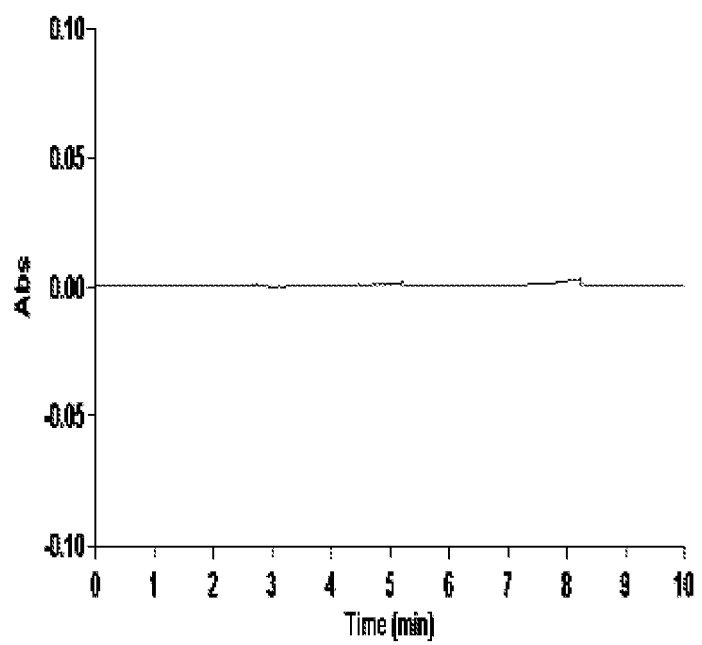
FIG. 6A and FIG. 6B shows the traces in the dynamic precipitation model for the evaluation of the 2 mg/mL CEM-101/Mannitol/Tartrate Formulation (CEM-101) in 0.5% lactate buffer at pH 4 in 0.5% saline at infusion rates of 1 mL/min (t=1 min), 2 mL/min (t=4 min) and 3 mL/min (t=7 min) and the comparison with the 2 mg/mL CEM-101/Mannitol/Tartrate Formulation (CEM-101) in 0.45% saline.
Figure 6B:
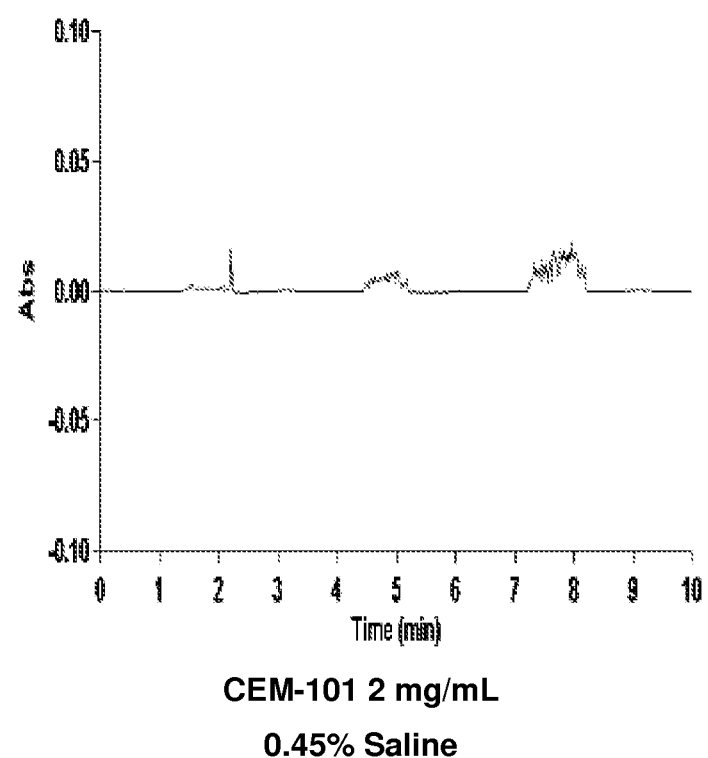
Figure 7:
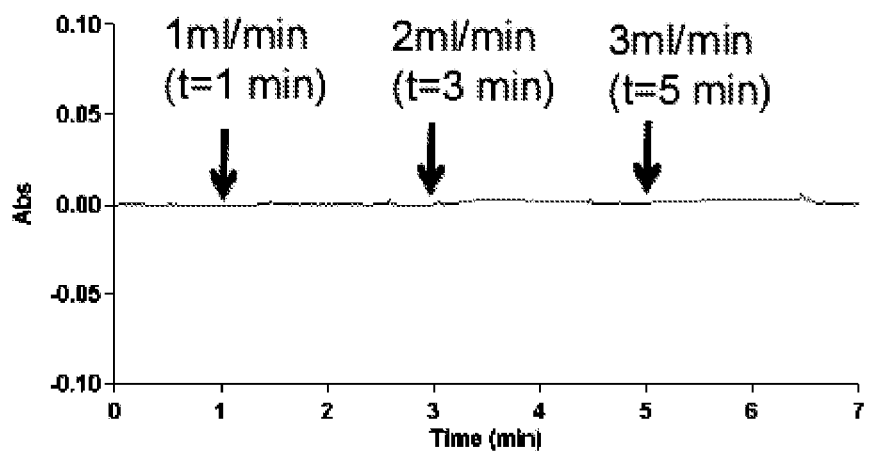
FIG. 7 shows the traces in the dynamic precipitation model for the evaluation of the 2 mg/mL and the 1 mg/mL CEM-101/Mannitol/Tartrate Formulation (CEM-101) in 1% lactate buffer at pH 4 in 0.45% saline at infusion rates of 1 mL/min (t=1 min), 2 mL/min (t=3 min) and 3 mL/min (t=5 min).
Figure 7:
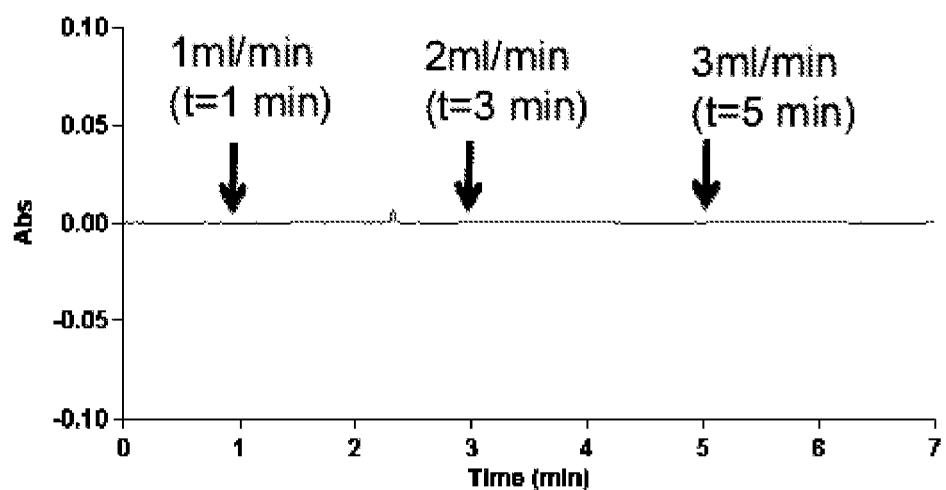
Figure 8:
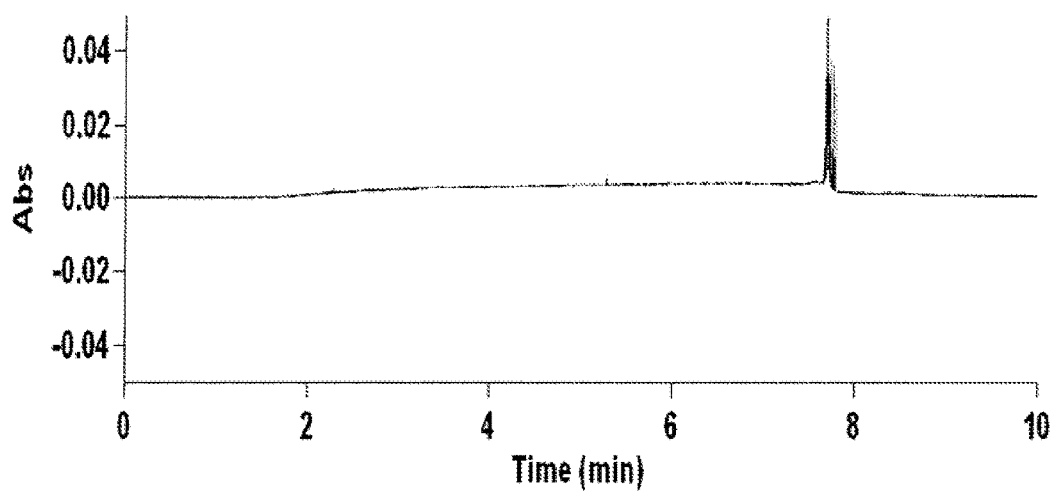
FIG. 8 shows the traces in the dynamic precipitation model for the evaluation of 3 mL/min (t=6.5 min) of 2 mg/mL SOL in 25 mM histidine+25 mM glutamic acid+25 mM acetic acid formulation at pH 5.0, each into a 0.5% saline vehicle.

In one illustrative embodiment of the invention, a solid pharmaceutical composition comprising a drug or other therapeutic agent that is characterized as having low solubility and/or low basicity is described. In one aspect, the formulation comprises lactic acid lactic acid or a pharmaceutically acceptable salt thereof, or a combination thereof. In one variation, the formulation comprises one or more amino acids or pharmaceutically acceptable salts thereof, or a combination thereof. In another variation, the formulation comprises lactic acid lactic acid or a pharmaceutically acceptable salt thereof, and one or more amino acids or pharmaceutically acceptable salts thereof, or a combination thereof. In another embodiment, the solid formulations are adapted for parenteral administration, such as intravenous administration. For example, the solid formulations may be reconstituted, or dissolved in a pharmaceutically acceptable vehicle for parenteral administration, such as intravenous administration.

In another illustrative embodiment, a solid pharmaceutical composition comprising a SOL, related compounds, and/or pharmaceutically acceptable salts thereof, is described. In one aspect, the formulation comprises lactic acid lactic acid or a pharmaceutically acceptable salt thereof, or a combination thereof. In one variation, the formulation comprises one or more amino acids or pharmaceutically acceptable salts thereof, or a combination thereof. In another variation, the formulation comprises lactic acid lactic acid or a pharmaceutically acceptable salt thereof, and one or more amino acids or pharmaceutically acceptable salts thereof, or a combination thereof. In another embodiment, the solid formulations are adapted for parenteral administration, such as intravenous administration. For example, the solid formulations may be reconstituted, or dissolved in a pharmaceutically acceptable vehicle for parenteral administration, such as intravenous administration.

In another illustrative embodiment of the invention, a liquid and/or solution pharmaceutical composition comprising a drug or other therapeutic agent that is characterized as having low solubility and/or low basicity is described. In one aspect, the formulation comprises lactic acid lactic acid or a pharmaceutically acceptable salt thereof, or a combination thereof. In one variation, the formulation comprises one or more amino acids or pharmaceutically acceptable salts thereof, or a combination thereof. In another variation, the formulation comprises lactic acid lactic acid or a pharmaceutically acceptable salt thereof, and one or more amino acids or pharmaceutically acceptable salts thereof, or a combination thereof. In another embodiment, the liquid and/or solution formulations further comprises a carrier or vehicle, such as water.

In another illustrative embodiment, a liquid and/or solution pharmaceutical composition comprising a SOL, related compounds, and/or pharmaceutically acceptable salts thereof, is described. In one aspect, the formulation comprises lactic acid lactic acid or a pharmaceutically acceptable salt thereof, or a combination thereof. In one variation, the formulation comprises one or more amino acids or pharmaceutically acceptable salts thereof, or a combination thereof. In another variation, the formulation comprises lactic acid lactic acid or a pharmaceutically acceptable salt thereof, and one or more amino acids or pharmaceutically acceptable salts thereof, or a combination thereof. In another embodiment, the liquid and/or solution formulations further comprises a carrier or vehicle, such as water.

In another embodiment, the formulations described herein include one or more compounds of the formula:

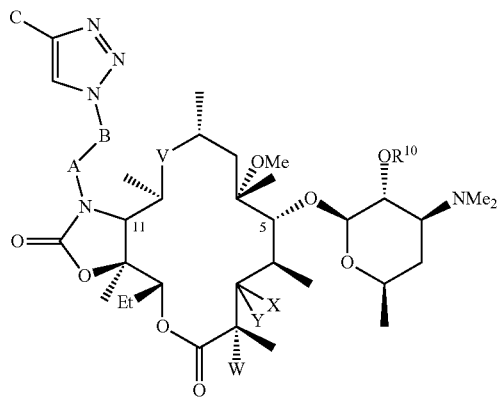

and pharmaceutically acceptable salts thereof, wherein:

$R^{10}$ is hydrogen, acyl or a prodrug moiety;

X and Y are taken together with the attached carbon to form carbonyl;

V is C(O);

W is H, F, Cl, Br, I, or OH;

A is $CH_2$, C(O), C(O)O, C(O)NH, $S(O)_2$, $S(O)_2NH$, or $C(O)NHS(O)_2$;

B is $C_2$-$C_{10}$ alkenylene, or B is $C_1$-$C_{10}$ alkylene, such as $(CH_2)_n$ where n is an integer ranging from 1-10, from 2-6, from 3-5, from 3-4, or n is 3; and C is hydrogen, hydroxy, acyl, acyloxy, sulfonyl, ureido, or carbamoyl, or alkyl, alkoxy, heteroalkyl, heteroalkoxy, aryl, arylalkyl, heteroaryl, or heteroarylalkyl, each of which is optionally substituted.

In another embodiment, $R^{10}$ is hydrogen. In another embodiment, W is H or F. In another embodiment, W is F. In another embodiment, A is $CH_2$. In another embodiment, B is $(CH_2)_n$, where n is an integer ranging from 1-10. In another embodiment, B is $(CH_2)_n$, where n is an integer ranging from 2-6. In another embodiment, B is $(CH_2)_n$, where n is an integer ranging from 3-5. In another embodiment, B is $(CH_2)_n$, where n is 3. In another embodiment, C is optionally substituted aryl. In another embodiment, C is aminoaryl. In another embodiment, C is 3-aminophenyl. It is to be understood that the selections for each of $R^{10}$ X, Y, V, W, A, B, and C combined in all possible ways area also described herein. For example, in another embodiment, $R^{10}$ is hydrogen, and W is H or F; and $R^{10}$ is hydrogen, W is F, and A is $CH_2$. In addition, it is to be understood that pharmaceutically acceptable salts of any of the foregoing are also described herein.

In another embodiment, the formulations described herein include a compound of the formula:

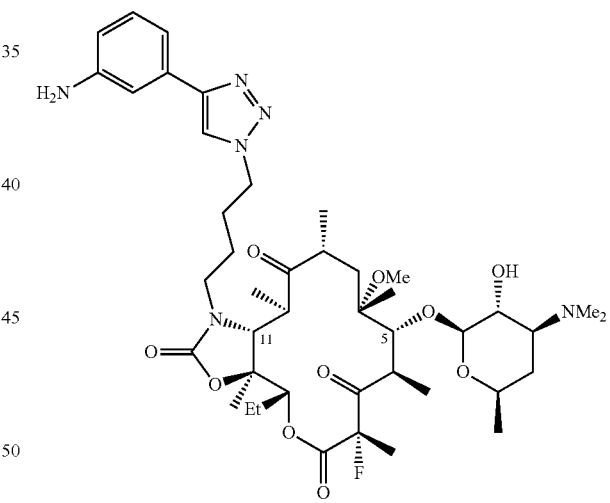

and pharmaceutically acceptable salts, hydrates, solvates, esters, and prodrugs thereof. The following acid dissociation constants are observed for SOL, pKa1=9.44; pKa2=3.5. Such dissociation constants are illustrative of compounds that may be characterized as having low basicity.

Several illustrative embodiments of the invention are described by the following enumerated clauses:

1. A pharmaceutical composition adapted for parenteral administration comprising one or more antibiotic compounds and a formulating agent, wherein the formulating agent is selected from the group consisting of lactic acid, an amino acid, and combinations thereof, and pharmaceutically acceptable salts of the foregoing; and where the one or more antibiotic compounds are of the formula

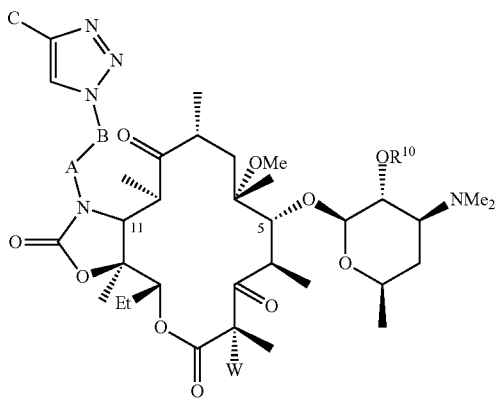

and pharmaceutically acceptable salts thereof, wherein:
$R^{10}$ is hydrogen, acyl or a prodrug moiety;
W is H, F, Cl, Br, I, or OH;
A is $CH_2$, C(O), C(O)O, C(O)NH, $S(O)_2$, $S(O)_2NH$, or $C(O)NHS(O)_2$;
B is $C_2$-$C_{10}$ alkenylene, or $C_1$-$C_{10}$ alkylene; and
C is hydrogen, hydroxy, acyl, acyloxy, sulfonyl, ureido, or carbamoyl, or alkyl, alkoxy, heteroalkyl, heteroalkoxy, aryl, arylalkyl, heteroaryl, or heteroarylalkyl, each of which is optionally substituted.

2. The composition of clause 1 wherein $R^{10}$ is hydrogen.

3. The composition of any one of clauses 1 or 2 wherein W is H or F.

4. The composition of any one of clauses 1 to 3 wherein W is F.

5. The composition of any one of clauses 1 to 4 wherein A is $CH_2$.

6. The composition of any one of clauses 1 to 5 wherein B is $C_1$-$C_{10}$ alkylene.

6.1. The composition of any one of clauses 1 to 5 wherein B is $C_2$-$C_6$ alkylene.

6.2. The composition of any one of clauses 1 to 5 wherein B is $C_3$-$C_6$ alkylene.

6.3. The composition of any one of clauses 1 to 5 wherein B is $C_3$-$C_5$ alkylene.

6.4. The composition of any one of clauses 1 to 5 wherein B is $C_3$-$C_4$ alkylene.

6.5. The composition of any one of clauses 1 to 5 wherein B is $C_4$ alkylene.

6.6. The composition of any one of clauses 1 to 5 wherein B is $C_3$ alkylene.

6.7 The composition of any one of clauses 1 to 6 wherein B is $(CH_2)_n$, where n is an integer from 1 to 10.

7. The composition of any one of clauses 1 to 6.1 wherein B is $(CH_2)_n$, where n is an integer from 2 to 6.

8. The composition of any one of clauses 1 to 6.3 wherein B is $(CH_2)_n$, where n is an integer from 3 to 5.

8.1 The composition of any one of clauses 1 to 6.4 wherein B is $(CH_2)_n$, where n is an integer from 3 to 4.

9. The composition of any one of clauses 1 to 6.4 wherein B is $(CH_2)_3$.

10. The composition of any one of clauses 1 to 9 wherein C is optionally substituted aryl.

10.1. The composition of any one of clauses 1 to 9 wherein C is optionally substituted phenyl.

11. The composition of any one of clauses 1 to 9 wherein C is aminoaryl.

11.1 The composition of any one of clauses 1 to 9 wherein C is aminophenyl.

12. The composition of any one of clauses 1 to 9 wherein C is 3-aminophenyl.

13. The composition of clause 1 wherein one of the compounds is solithromycin, or a pharmaceutically acceptable salt thereof.

14. The composition of any one of clauses 1 to 13 wherein the formulating agent is lactic acid or a pharmaceutically acceptable salt thereof, or a combination thereof.

14.1 The composition of any one of clauses 1 to 13 wherein the formulating agent is lactic acid or a sodium salt of a lactic acid, or a combination thereof.

15. The composition of clause 14 wherein the lactic acid or the sodium salt comprises any mixture of L-lactic acid and D-lactic acid and the sodium salts thereof.

16. The composition of clause 14 wherein the lactic acid or the sodium salt is L-lactic acid or the sodium salt thereof.

17. The composition of clause 14 wherein the lactic acid or the sodium salt is DL-lactic acid or the sodium salt thereof.

18. The composition of any one of clauses 1 to 17 wherein the formulating agent is one or more amino acids, or pharmaceutically acceptable salts thereof, or a combination thereof.

19. The composition of any one of clauses 1 to 17 wherein the formulating agent is one or more alpha amino acids, or pharmaceutically acceptable salts thereof, or a combination thereof.

20. The composition of any one of clauses 1 to 17 wherein the formulating agent is one or more amino acids selected from the naturally occurring amino acids and stereoisomers thereof, and pharmaceutically acceptable salts of the foregoing, and combinations thereof.

21. The composition of any one of clauses 1 to 17 wherein the formulating agent is one or more amino acids selected from the naturally occurring amino acids having the natural configuration, and pharmaceutically acceptable salts thereof, and combinations thereof.

22. The composition of any one of clauses 1 to 17 wherein the formulating agent is one or more amino acids selected from the naturally occurring amino acids having the natural configuration that have side chain functional groups that are ionizable under physiological conditions, and pharmaceutically acceptable salts thereof, and combinations thereof.

23. The composition of any one of clauses 1 to 17 wherein the formulating agent is histidine, aspartic acid, glutamic acid, or pharmaceutically acceptable salts thereof, or combinations thereof.

24. The composition of any one of clauses 1 to 17 wherein the formulating agent is histidine or a pharmaceutically acceptable salt thereof, or a combination thereof.

25. The composition of any one of clauses 1 to 17 wherein the formulating agent is aspartic acid or a pharmaceutically acceptable salt thereof, or a combination thereof.

26. The composition of any one of clauses 1 to 17 wherein the formulating agent is glutamic acid or a pharmaceutically acceptable salt thereof, or a combination thereof.

27. The composition of any one of clauses 1 to 17 wherein the formulating agent is histidine or a pharmaceutically acceptable salt thereof, and aspartic acid or a pharmaceutically acceptable salt thereof, or a combination thereof.

28. The composition of any one of clauses 1 to 17 wherein the formulating agent is histidine or a pharmaceutically acceptable salt thereof, and glutamic acid or a pharmaceutically acceptable salt thereof, or a combination thereof.

29. The composition of any one of clauses 1 to 17 wherein the formulating agent is aspartic acid or a pharmaceutically acceptable salt thereof, and glutamic acid or a pharmaceutically acceptable salt thereof, or a combination thereof.

30. The composition of any one of clauses 1 to 17 wherein the formulating agent is histidine or a pharmaceutically acceptable salt thereof, aspartic acid or a pharmaceutically acceptable salt thereof, and glutamic acid or a pharmaceutically acceptable salt thereof, or a combination thereof.

31. The composition of any one of the preceding clauses prepared by lyophilizing an aqueous solution thereof.

31.1. The composition of any one of clauses 1 to 31 further comprising a liquid vehicle.

31.2. The composition of clause 31.1 wherein the liquid vehicle comprises water.

31.3. The composition of any one of clauses 31.1 to 31.2 wherein the liquid vehicle contains less than about 0.9% saline.

31.4. The composition of any one of clauses 31.1 to 31.3 wherein the liquid vehicle contains less than about 0.45% saline.

31.5. The composition of any one of clauses 31.1 to 31.4 wherein the liquid vehicle is substantially free of sodium chloride.

31.6. The composition of any one of clauses 31.1 to 31.5 wherein the liquid vehicle is substantially free of citric acid or a salt thereof.

31.7. The composition of any one of clauses 31.1 to 31.6 wherein the liquid vehicle comprises mannitol.

32. The composition of any one of clauses 1 to 17 wherein the formulation has a pH in the range from about 3.5 to about 6.

32.1. The composition of any one of clauses 1 to 17 wherein the formulation has a pH in the range from about 4 to about 6.

32.2. The composition of any one of clauses 1 to 17 wherein the formulation has a pH in the range from about 4 to about 5.5.

32.3. The composition of any one of clauses 1 to 17 wherein the formulation has a pH in the range from about 4.2 to about 5.5.

32.4. The composition of any one of clauses 1 to 17 wherein the formulation has a pH in the range from about 4 to about 5.

32.5. The composition of any one of clauses 1 to 17 wherein the formulation has a pH in the range from about 4.2 to about 5.

32.6. The composition of any one of clauses 1 to 17 wherein the formulation has a pH in the range from about 4.2 to about 4.5.

32.7. The composition of any one of clauses 1 to 17 wherein the formulation has a pH of about 4.5.

32.8. The composition of any one of clauses 1 to 17 wherein the formulation has a pH of about 4.2.

33. A kit comprising a composition of any one of clauses 1 to 32.8, and instructions for the preparation of a pharmaceutically acceptable infusion solution thereof.

34. A method for treating a patient having a bacterial infection, the method comprising the step of parenterally administering to the patient a therapeutically effective amount of a composition of any one of clauses 1 to 32.8.

35. The method of clause 34 wherein the administering step is performed by intravenous injection.

In reciting the foregoing collection of clauses, it is to be understood that all possible combinations of features, and all possible subgenera and subcombinations are described.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carboxylic acid and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $-(CH_2)_x Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from $-CO_2R^4$ and $-CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl and optionally substituted heteroaryl$(C_2-C_{16})$alkanoyl, such as the aryl or heteroaryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

Accordingly, it is to be understood herein that the source of the drug or therapeutic agent, such as SOL, is not limiting. For example, SOL may be included in the formulations described herein starting from its neutral form, or one or more salt forms. Alternatively, SOL may be included in the formulations described herein starting from a reconstitutable form, such as any of the various lyophilized forms of SOL, including CEM-101 lyo, compositions described in PCT international application serial No. US2011/027984, the disclosure of which is incorporated herein by reference. Further, in any of the foregoing, the SOL may be included in the formulations described herein starting from any morphological form, such as amorphous, Form I, Form II, and the like, such as described in PCT international application serial Nos. US2004/006645 and US2011/029424, the disclosures of each of which are incorporated herein by reference.

In another embodiment, the compound used in the compositions described herein is SOL. In another embodiment, the SOL is neutral. In another embodiment, the SOL is amorphous. In another embodiment, the SOL is Form I. In another embodiment, the SOL is Form II. In another embodiment, the SOL is a pharmaceutically acceptable salt. In another embodiment, the SOL is a tartrate salt. In another embodiment, the SOL is a hydrochloride salt. In another embodiment, the SOL is lyophilizate comprising SOL, mannitol, and tartaric acid. In another embodiment, the SOL is lyophilizate comprising SOL, histidine, glutamic acid, and aspartic acid.

In another embodiment, the formulation comprises an amino acid. Illustrative amino acids that may be included in the solid, solution or liquid formulations described herein include any alpha or beta amino acid, and pharmaceutically acceptable salts thereof. In one embodiment, the amino acids are selected from the naturally occurring amino acids and stereoisomers thereof, and pharmaceutically acceptable salts of the foregoing. In another embodiment, the amino acids are selected from the naturally occurring amino acids having the natural configuration, and pharmaceutically acceptable salts thereof. In another embodiment, the amino acids are selected from the naturally occurring amino acids having the natural configuration that have side chain functional groups that are ionizable under physiological conditions, and pharmaceutically acceptable salts thereof. In another embodiment, the amino acids are selected from histidine, aspartic acid, glutamic acid, and pharmaceutically acceptable salts thereof.

In another embodiment, the solid, solution or liquid formulations described herein include histidine, such as L-(−)-histidine, and pharmaceutically acceptable salts thereof. In another embodiment, the solid, solution or liquid formulations described herein include glutamic acid, such as L-(+)-glutamic acid, and pharmaceutically acceptable salts thereof. In another embodiment, the solid, solution or liquid formulations described herein include aspartic acid, such as L-(+)-aspartic acid, and pharmaceutically acceptable salts thereof. In another embodiment, the solid, solution or liquid formulations described herein include lactic acid, such as L-lactic acid and DL-lactic acid, and pharmaceutically acceptable salts thereof. In another embodiment, the solid, solution or liquid formulations described herein include mannitol, such as D-(+)-mannitol.

In another embodiment, described herein are solid formulations of the compounds described herein that are adapted for reconstitution into a carrier or vehicle. In another embodiment, the solid formulation comprises SOL, histidine, glutamic acid, and aspartic acid.

The term "administering" as used herein includes all means of introducing liquid or solution formulations of compounds and compositions described herein to the patient, including, but are not limited to, oral (po), intravenous (iv), intramuscular (im), subcutaneous (sc), transdermal, ocular, vaginal, rectal, and the like. The compounds and compositions described herein may be administered in unit dosage forms and/or formulations containing conventional nontoxic pharmaceutically-acceptable carriers, adjuvants, and vehicles.

Depending upon the disease as described herein, the compounds and compositions described herein may be administered locally or systemically.

Illustratively, administering includes local use, such as when administered locally to the site of disease, injury, or defect. Illustrative local administration may be performed during open surgery, or other procedures when the site of disease, injury, or defect is accessible. Local administration may be performed using parenteral delivery where the compound or compositions described herein are deposited locally to the site without general distribution to multiple other non-target sites in the patient being treated. It is further appreciated that local administration may be directly in the disease site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes for parenteral administration include intravenous, intraarterial, intraperitoneal, epidurial, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

Parenteral Compositions. The parenteral pharmaceutical composition may be administered by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), in vials containing several doses and in which a suitable preservative may be added (see below), or in prefilled syringes.

As indicated above, the pharmaceutical compositions described herein may be in the form suitable for sterile injection. To prepare such a composition, the suitable active drug(s) are dissolved or suspended in a parenterally acceptable liquid vehicle. Illustrative vehicles and solvents include, but are not limited to, water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like. In addition, the carriers may also include any combination of tonicity agents, including but not limited to, mannitol, such as 3-5% mannitol, 3% mannitol, 4% mannitol, 4.3% mannitol, and 5% mannitol, phosphate, acetate, additional tartrate, saline, such as physiological saline (0.9%), ½ physiological saline (0.45%), and 0.5% saline, and the like.

In another embodiment, the parenteral formulation is a hypotonic mannitol formulation. In another embodiment, the parenteral formulation is a isotonic mannitol formulation. In another embodiment, the parenteral formulation has an osmolality of about 250 or less. In another embodiment, the parenteral formulation has an osmolality of about 250 or less. In another embodiment, the parenteral formulation has an osmolality of about 350 or less.

The pH of the solution or liquid formulations described herein may be at any of a wide range of physiologically acceptable or pharmaceutically acceptable values. Illustratively, the pH is in the range from about 2 to about 8, from about 3 to about 7, from about 4 to about 6.5, and the like. In another embodiment, the pH of the solution or liquid formulations described herein is near neutral. In another embodiment, the pH of the solution or liquid formulations described herein is in the range from about 4 to about 6, from about 4 to about 5.5, from about 4 to about 5, from about 4 to about 4.5, from about 4.5 to about 6.5, from about 4.5 to about 6, from about 4.5 to about 5.5, or from about 4.5 to about 5.

Depending upon the needs of the patient, and the clinical conditions, administration of a drug by the iv route is may be favored for a number of different reasons, including rapid introduction into the systemic circulation and high bioavailability and other advantages obtained by avoiding issues of stability in the gastrointestinal tract, absorption, distribution and metabolic or toxic effects involving the liver on oral administration. However, the solubility of the drug in blood may limit the concentration or rate at which it may be administered by the intravenous route.

Without being bound by theory, it is believed herein that if the drug separates from the phase formed by the constituents of its vehicle and the blood in which it is injected, a phase of oily droplets or crystals may be formed in the veins. The separated phase may redissolve in the blood relatively rapidly, resulting is only a slight delay in bioavailability without loss of efficacy. Otherwise, the effect may be uneven or delayed bioavailability. Without being bound by theory, it is also believed herein that precipitation of the therapeutic agent as crystalline particles can cause cellular abrasion as the particles move along the wall of the vein, an effect which is purely physical and not pharmacological. Phlebitis, an inflammation of the vein wall, has been associated with effects of particulate matter associated with iv injection. Under conventional conditions of administration, in which the injection rate of a parenteral drug does not exceed the blood flow rate, this problem may be overcome by reducing the concentration of the therapeutic agent in the injection vehicle or by extending the time of the injection, each of which is an undesirable change. Alternatively, modification of the formulation of the composition of the injected drug may ameliorate the problem.

Without being bound by theory, it is also believed herein that injection phlebitis can be caused by a number of different factors including pH, tonicity, particulate matter, and precipitation upon dilution in the bloodstream (see, for example, Ward et al., 1993. Studies in Phlebitis VI: Dilution-Induced Precipitation of Amidoarone HCl. Journal of Parenteral Science and Technology. 47(4). 161-165). Injection of drugs formulated above or below pH 7.4 may result in an exponential decrease in solubility with dilution. This can overcome the linear decrease in concentration upon dilution, thereby producing precipitation (see, for example, Narazaki et al., 2007. Estimation of Precipitation Upon Dilution of pH-Controlled Formulations. Molecular Pharmaceutics. 4(4), 550-555). Using a buffer may inhibit precipitation by minimizing the pH increase in the vicinity of the injected basic drug in blood. On the other hand, using a buffer may lead to the formation of an insoluble salt between the drug and the acid buffer ion.

Although a number of animal models have been developed for measuring in vivo precipitation and in vivo phlebitis, it may be desirable to utilize quantitative in vitro models to measure precipitation upon injection of a therapeutic agent (see, for example, Yalkowsky et al., 1998. Journal of Pharmaceutical Sciences, 87(7), 787-796). For example, an apparatus and a dynamic precipitation model using isotonic Sorensen's phosphate buffer (ISPB) as the blood surrogate has been described (see, for example, Johnson et al., 2003 Prediction of Precipitation-Induced Phlebitis: A Statistical Validation of an In Vitro Model. Journal of Pharmaceutical Sciences, 92(8), 1574-1581).

In the dynamic precipitation model described in detail herein, solutions of test compound, such as SOL, as a tartrate buffered solution of greater than or equal to 1 mg/mL of SOL in 0.45% saline, administered at approximately 1 mL/min or faster, may exhibit precipitation. This precipitation suggests that intravenous injection of SOL at concentrations and infusion rates higher than about 1 mg/mL at about 1 mL/min may be associated with precipitation resulting in pain associated with precipitation induced phlebitis. Therefore, to avoid such precipitation, the rate of administration requires, for example, almost seven hours for the administration of a dose of 400 mg of SOL. Thus, there is needed a pharmaceutical composition which enables administration of SOL at a higher concentration and/or a higher rate for clinical use.

Azithromycin, administered in the dynamic precipitation model as a citrate buffered solution in 0.45% saline at 2 mg/mL and 4 mL/min, does not exhibit precipitation; so the pain which is observed upon intravenous injection of azithromycin most likely is not attributable to precipitation. Instead, it has been reported that the pain observed with azithromycin injection may be pharmacologic pain. However, SOL has been discovered to not exhibit pharmacologic pain. Nevertheless, SOL similarly formulated in citrate buffer may cause pain. Without being bound by theory, it is believed herein that although citrate has three buffering carboxylate units, SOL may yet exhibit precipitation at concentrations and infusion rates higher than about 1 mg/mL at about 1 mL/min.

An intravenous infusion solution of SOL and related compounds suitable for treatment in a disease such as moderately severe to severe community acquired bacterial pneumonia (CABP) is needed. Toxicology studies of 28 days in dog and monkey, dosing a tartrate-buffered solution of 1 mg/mL of SOL in 3% mannitol infused at approximately 1 mL/min, are successfully complete without evidence of pain or other adverse events. However, without being bound by theory, it is believed herein that infusion at higher concentrations and/or at higher rates of infusion, which are highly desirable in the clinical setting, may not be practical with current formulations due to the substantially lower solubility observed with SOL and related compounds compared to other macrolide, enolide, and ketolide compounds.

It has been found, surprisingly, that use of lactate formulating agents greatly improves the solubility of solithromycin. Accordingly, provided herein are pharmaceutical compositions comprising lactate formulating agents adapted for the parenteral administration of the fluoroketolide antibiotic SOL and related compounds, as well as methods for their use in the treatment of bacterial, protozoal, and other infections.

It has also been found, surprisingly, that use of amino acid formulating agents greatly improves the solubility of solithromycin. Accordingly, provided herein are pharmaceutical compositions comprising amino acid formulating agents adapted for the parenteral administration of the fluoroketolide antibiotic SOL and related compounds, as well as methods for their use in the treatment of bacterial, protozoal, and other infections.

Although it is to be understood herein that solithromycin itself may not cause pharmacologic pain, changes in the solubility and solution characteristics of solithromycin solutions may cause pain due to, for example, precipitation. As further described below, to evaluate the potential for pain related to such an iv infusion at doses and rates which are comparable to the usual hospital use with azithromycin, iv infusion solutions of SOL are evaluated in a rabbit ear vein model, using azithromycin for injection for comparison. It is found that iv infusion solutions of SOL formulations as described herein are well accepted in single dose and multiple dose studies using the rabbit ear vein model. In contrast, azithromycin for injection caused considerable pain at the concentration and infusion rate of the usual hospital use.

It has been discovered that a dramatic reduction in precipitation is observed with the use of lactate buffer in the formulations of SOL for intravenous administration as determined by the dynamic precipitation model. It has also been discovered that a dramatic reduction in precipitation is observed with the use of amino acid buffers in the formulations of SOL for intravenous administration as determined by the dynamic precipitation model.

As shown in the Examples described herein, using the dynamic precipitation model, when SOL and related compounds are administered at 3 mg/mL in 0.45% saline, precipitation is noted at rates greater than or equal to 1.0 mL/min. At the lower concentrations, 2 or 1 mg/mL in 0.45% saline, precipitation is noted at rates greater than 1.0 mL/min, and 1.0 mL/min is borderline. The amounts of precipitation in 5% mannitol are similar to those in 0.45% saline without the added mannitol.

In contrast, when using SOL and related compounds in both 0.5% and 1% lactate buffer (pH 4) in 0.45% saline, precipitation in the model is reduced below the delineating opacity value for determining precipitation with phlebitic potential at 1 mg/mL and 2 mg/mL at a rate of 3 mL/min. The use of either L-lactate buffer or DL-lactate buffer reduced precipitation in all cases. However, using 0.5, 1 and 5 mM citrate buffer (pH 4) in 0.45% saline does not significantly reduce precipitation in the dynamic precipitation model at concentrations of 2 mg/mL and 3 mg/mL SOL. Similarly, 10 or 25 mM tartrate buffer (pH 4) in 0.45% saline does not significantly reduce precipitation in the dynamic precipitation model at concentrations of 2 mg/mL and 3 mg/mL SOL. Addition of a citrate or tartrate co-buffer to the lactate buffer had minimal effect in the dynamic precipitation model. In all cases in which precipitation is observed, the amount of precipitation, as reflected by the amount of absorbance, increases with the injection rate and concentration.

In addition, when using SOL/amino acid formulations in various lactate, phosphate and acetate buffers, at various pH levels, in a suitable tonicity carrier, such as 0.45% saline, 3-5% mannitol, and the like, precipitation in the model is reduced below the delineating opacity value for determining precipitation with phlebitic potential at 1 mg/mL and 2 mg/mL at a rate of 3 mL/min.

Azithromycin and clarithromycin have been approved for i.v. administration. However, their use has been reportedly limited due to inflammation, pharmacologic pain, hepatotoxicity, and/or adverse cardiac effects, such as QT prolongation. It is appreciated herein that such side effects are exacerbated by the higher exposure that occurs from parenteral administration compared to oral administration. For example, clarithromycin reportedly accumulates in cardiac tissue. In addition, though azithromycin does not cause high cardiac tissue exposure, azithromycin reportedly has high potency in causing QT prolongation, such that even minimal exposure precautions may be necessary. Ketolides, such as telithromycin are reportedly particularly not suitable for parenteral, such as i.v, administration due to unwanted side effects.

It has been unexpectedly discovered herein that the triazole-containing ketolide compounds and compositions described herein do not elicit significant pharmacologic pain, hepatotoxicity, or cardiac effects, such as QT prolongation. Described herein are compositions adapted for parenteral, including i.v., administration that are pain free, or substantially pain free. Described herein are compositions adapted for parenteral, including i.v., administration that do not cause, or do not substantially cause hepatotoxicity. Described herein are compositions adapted for parenteral, including i.v., administration that are free of, or substantially free of adverse cardiac effects, such as QT prolongation. Described herein are compositions adapted for parenteral, including i.v., administration that do not cause, or do not substantially cause inflammation.

The following examples further illustrate specific embodiments of the invention; however, the following illustrative examples should not be interpreted in any way to limit the invention.

EXAMPLES

Example

Any source of SOL may be used in preparing the formulations described herein. Illustratively, the source of SOL is a reconstitutable lyophilizate, as also generally described in WO 2011/112864. Illustratively, the source of SOL is a reconstitutable lyophilizate prepared from the following aqueous solution. The theoretical quantities include 6% excess to cover overfill. The density of SOL solution is approximately 1.030 g/mL.

|  | % w/w | Qty/Vial (mg/5 mL) | Theoretical |
|---|---|---|---|
| SOL | 5.0 | 250 | 0.53 |
| Mannitol, USP (Pearlitol PF) | 5.0 | 250 | 0.53 |
| L(+)-Tartaric Acid, USP | 0.6 | 29 | 61.5 |
| Sodium Hydroxide, USP | — | — | For pH adjustment (e.g. to pH 4) |
| Water for Injection (WFI), USP | q.s to 100% | q.s. to 5 mL | q.s. to 10.9 kg |
| TOTAL | 100 | 5.2 g (5 mL) | 10.9 kg |

Example

SOL from any source may be directly dissolved into a formulation solution described herein. Illustratively, the following final formulation comprises 150 mM Histidine, 150 mM Glutamic Acid, and 150 mM Aspartic Acid, at pH 4.5.

Example

SOL from any source may be directly dissolved into a formulation solution described herein. Illustratively, the following formulation agents are used in preparing the pharmaceutical compositions described herein. The density of 150 mM histidine, 150 mM glutamic acid, and 150 mM aspartic acid solution at ambient temperature is approximately 1.027 g/mL.

|  | % w/v | Qty/Vial (g/25 mL) | Theoretical (kg) |
|---|---|---|---|
| L-Histidine, USP | 2.3% | 0.58 | 0.98 |
| L-Aspartic Acid, USP | 2.0% | 0.50 | 0.84 |
| L-Glutamic Acid, FCC Multicompendial (BP & EP) | 2.2% | 0.55 | 0.93 |
| Sodium Hydroxide, NF | — | — | For pH adjustment |
| Hydrochloric Acid, NF | — | — | For pH adjustment |
| Water for Injection (WFI), USP | q.s to 100% | q.s. to 25 mL | q.s. to 43 kg |
| TOTAL | 100 | 26 g (25 mL) | 43 kg |

Example

Any source of SOL may be used in preparing the formulations described herein. Illustratively, the source of SOL is a reconstitutable lyophilizate prepared from the following aqueous solution. The theoretical quantities include 7% to cover overfill. The water for injection is removed during lyophilization. The density of the filling solution is approximately 1.041 g/ml. The final target pH of the formulation is 4.5.

|  | % w/w | Quantity per Vial (mg) | Theoretical Quantity per Batch (g) |
|---|---|---|---|
| SOL | 1.9 | 428 | 642 |
| L-Histidine, USP, EP | 2.8 | 623 | 934 |
| L-Glutamic Acid, FCC Multicompendial (BP & EP) | 2.7 | 590 | 886 |
| L-Aspartic Acid, USP, EP | 2.4 | 534 | 801 |
| Sodium Hydroxide, NF | NA | pH adjustment | pH adjustment |
| Hydrochloric Acid, NF | NA | pH adjustment$^e$ | pH adjustment$^e$ |
| Water for Injection$^e$ (WFI), USP | QS | QS | QS |
| Total | 100 | 2230 | 33400 |

Example

Saline vehicles are prepared from 0.9% sodium chloride injection, USP, or diluted to 0.45% with water for injection. All formulations are optionally filtered using a 0.45 µM filter, such as an Alltec 0.45 µM filter.

Method Example

Dynamic Precipitation Model. The dynamic precipitation apparatus is shown in FIG. 1, and is also described in Johnson et al., (2003). The apparatus includes a predetermined distance, illustratively a 15 cm distance, between the tip of the injection needle and the UV flow cell, and three main components to simulate blood flow and different infusion rates of drug. Illustratively, a Cole-Palmer-Masterflex® 7520-00 peristaltic pump is used to direct the flow of blood surrogate at 5 mL/min. Illustratively, a Harvard Apparatus Precision Syringe Pump 22 is used to infuse drug formulations into the system at various injection rates. Illustratively, a Cary UV-50 Bio Spectrophotometer with a 1.00 cm flow cell is used to monitor absorbance as a measure of precipitation in the formulation-blood surrogate system.

Each sample is prepared by dissolving test compound and formulation agents into water or vehicle, and adjusting the pH with either 1 M HCl or 1 M NaOH, as appropriate to the indicated final concentration of test compound. Lactic, citric, and tartaric acid formulation agent stock solutions are made by dissolving the predetermined weight of solid or liquid into water and adjusting pH with either 1 M HCl or 1 M NaOH.

The blood surrogate (Isotonic Sorensen's Phosphate Buffer, 0.067 M, pH 7.4) is pumped from a reservoir through Tygon® tubing (R-6306) fitted with 2 IV-set Y-injection sites that pass into the flow cell and terminate in a waste container. A Dwyer MMA-35 flow meter, along with a timer and graduated cylinder, is used to measure the rate of surrogate blood flow through the system. Illustratively, flow is 5 mL/min.

The test compound formulations are infused at different rates through the downstream second Y-injection site into the flow of the blood surrogate entering into the flow cell. A 0.001 M HCl solution is injected into the first Y-injection site following each infusion of test compound to flush the downstream tubing and flow cell. All injections are performed at 25° C. The spectrophotometer software (Cary UVWin) is set to read a constant absorbance, illustratively 500 nm, versus time.

Samples are made with buffer and drug concentrations as described. After the flow rate is confirmed at 5 mL/min, the spectrophotometer is set to record absorbance at 500 nm for 5-10 minutes, and injections are performed at different rates as specified. To prevent any residual precipitation build up in the tubing or flow cell, a flush of pH 3 HCl is performed between injections. The flow cell is optionally visually inspected between runs for the presence of precipitation. Static precipitation measurements are also optionally performed by a two-fold serial dilution of test compound formulation in blood surrogate using a laser pointer as a Tyndall beam to determine the presence of particulates.

An absorbance (opacity value) of 0.003 is considered to be the threshold level for detection and assessing precipitation having phlebitic potential. Control (placebo/vehicle) formulation shows absorbance of about 0.003 or less. An absorbance at or above 0.05 is considered to be the threshold level for assessing precipitation having phlebitic potential. An absorbance of about 0.05 or less is considered to be an acceptable potential for precipitation having phlebitic potential. An absorbance of about 0.03 or less is considered to be a low potential for precipitation having phlebitic potential. An absorbance of about 0.01 or less is considered to be a very low potential for precipitation having phlebitic potential.

The control vehicles, 0.45% saline and 5.0% mannitol, are tested and show BQL absorbance.

Comparative Example

SOL formulations using conventional excipients. Various SOL salts were dissolved in a vehicle and tested in the Dynamic Precipitation Model. All water was filtered through a Millipore Milli-Q water system dispensing water at 18M'Ω·cm resistivity. and was filtered using a 0.45 µm (Alltech) membrane filter. The pH was adjusted as needed with 1 M HCl, or 1 M NaOH. Azitromycin citrate and erythromycin lactobionate were each used as positive controls, and showed BQL (<0.003).

| Example | Concentration | Infusion Rate | pH | Vehicle | Absorbance |
|---|---|---|---|---|---|
| SOL | 3 mg/mL | 3 mL/min | 4.0 | 0.9% NaCl | − |
| SOL-citrate | 3 mg/mL | 3 mL/min | 4.0 | 5.0% mannitol | − |
| SOL-lactobionate | 2 mg/mL | 3 mL/min | 4.0 | 5.0% mannitol | ++ |
| SOL-tartrate | 2 mg/mL | 3 mL/min | 4.0 | 5.0% mannitol | ++ |
| SOL-oxalate | 2 mg/mL | 3 mL/min | 4.0 | 5.0% mannitol | ++ |
| SOL-gluconate | 2 mg/mL | 3 mL/min | 5.3 | 5.0% mannitol | +++ |
| erythromycin-lactobionate | 2 mg/mL | 3 mL/min | n/a | 0.9% NaCl | ++++ |
| Azitromycin citrate | 2 mg/mL | 4 mL/min | n/a | 0.45% NaCl | ++++ |

(−) = ≥0.05
(+) = <0.05
(++) = <0.03
(+++) = <0.01
(++++) = BQL of <0.003

Comparative Example

SOL at 2 mg/mL in 38.5 mM Tartaric Acid and 0.5% Monothioglycerol in 3% Mannitol at pH 4.0 injected at 2 mL/min, 3 mL/min, or 4 mL/min, with an infusion duration of 5 minutes, showed minimal precipitation.

Comparative Example

SOL at 2 mg/mL in 38.5 mM Tartaric Acid and in 5% Mannitol at pH 4.0 injected at 2 mL/min, 3 mL/min, or 4 mL/min with an infusion duration of 5 minutes, showed minimal precipitation.

Comparative Example

SOL at 2 mg/mL in 20 mM Tartaric Acid in 5% Mannitol at pH 4.2 injected at 3 mL/min with an infusion duration of 1 minute, showed minimal precipitation.

Comparative Example

SOL at 2 mg/mL in 10 mM Tartaric Acid in 5% Mannitol at pH 4.2 injected at 3 mL/min with an infusion duration of 1 minute, showed minimal precipitation.

Comparative Example

SOL at 3 mg/mL in 5 mM Tartaric Acid in 5% Mannitol at pH 4.2 injected at 2 mL/min or 3 mL/min was compared with SOL at 2 mg/mL in 5% Mannitol injected at 2 mL/min or 3 mL/min each with an infusion duration of 2 minutes. The addition of tartaric acid substantially decreases the amount of observed precipitation at both infusion rates.

Comparative Example

SOL at 3 mg/mL in 0.45% Saline vehicle: When infused at the injection rate of 0.3, 1.0, 3.0 and 6.0 mL/min (infusion started at t=1.0 min), precipitation is noted at rates greater than or equal to 1.0 mL/min, showing BQL, about 0.02, about 0.1, and about 0.3, respectively.

Comparative Example

SOL at 2 mg/mL in 0.45% Saline vehicle: When infused at the injection rate of 0.3, 1.0, 3.0 and 6.0 mL/min (infusion started at t=1.0 min), precipitation is noted at rates of 3.0 and 6.0 mL/min; and 1.0 mL/min is borderline, showing BQL, BQL, about 0.02, and about 0.1, respectively.

Comparative Example

SOL at 1 mg/mL in 0.45% Saline vehicle: When infused at the injection rate of 0.3, 1.0, 3.0 and 6.0 mL/min (infusion started at t=1.0 min), precipitation is noted at rates of 3.0 and 6.0 mL/min; and 1.0 mL/min is borderline, showing BQL, BQL, BQL, and about 0.1, respectively.

Comparative Example

SOL at 3 mg/mL in 5% Mannitol vehicle: When infused at the injection rate of 0.3, 1.0, 3.0 and 6.0 mL/min (infusion started at t=1.0 min), precipitation is noted at rates greater than or equal to 1.0 mL/min, showing BQL, about 0.1, about 0.4, and about 0.6, respectively.

Comparative Example

SOL at 2 mg/mL in 5% Mannitol vehicle: When infused at the injection rate of 0.3, 1.0, 3.0 and 6.0 mL/min (infusion started at t=1.0 min), precipitation is noted at rates greater than or equal to 1.0 mL/min, showing BQL, about 0.03, about 0.06, and about 0.1, respectively.

Comparative Example

SOL at 1 mg/mL in 5% Mannitol vehicle: When infused at the injection rate of 0.3, 1.0, 3.0 and 6.0 mL/min (infusion started at t=1.0 min), precipitation is noted at rates greater than or equal to 3.0 mL/min, showing BQL, BQL, 0.01, and about 0.05, respectively. Generally, the addition of mannitol decreases the observed amount of precipitation.

Example

Lactic acid based formulations. The following illustrative formulations are prepared using CEM-101 lyo (which includes the tartrate indicated as Buffer 1) where the effect of lactic acid is compared to 0.45% saline alone.

| Compound | (mg/mL) Drug | Buffer-1 | % | Buffer-2 | % | Saline % | pH |
|---|---|---|---|---|---|---|---|
| CEM-101 | 2 | Tartrate | 0.023 | | | 0.45 | |
| CEM-101 | 3 | Tartrate | 0.035 | | | 0.45 | |
| CEM-101 | 1 | Tartrate | 0.012 | L-lactate | 1.000 | 0.45 | 4.09 |
| CEM-101 | 2 | Tartrate | 0.023 | L-lactate | 1.000 | 0.45 | 4.09 |
| CEM-101 | 3 | Tartrate | 0.035 | L-lactate | 1.000 | 0.45 | 3.94 |

In each case, the addition of lactic acid decreases the observed amount of precipitation to BQL.

Example

Lactic acid based formulations including citrate. The following illustrative formulations are prepared using CEM-101 lyo (which includes the tartrate indicated as Buffer 1) where the effect of lactic acid is compared to 0.45% saline alone and citrate.

| Compound | (mg/mL) Drug | Buffer-1 | % | Buffer-2 | % | Saline % | pH |
|---|---|---|---|---|---|---|---|
| Azithromycin | 2 | Citrate | 0.153 | | | 0.45 | |
| CEM-101 | 2 | Tartrate | 0.023 | | | 0.45 | |
| CEM-101 | 3 | Tartrate | 0.035 | | | 0.45 | |
| CEM-101 | 2 | Tartrate | 0.023 | Citrate | 0.096 | 0.45 | 3.96 |
| CEM-101 | 3 | Tartrate | 0.035 | Citrate | 0.096 | 0.45 | 3.96 |
| CEM-101 | 1 | Tartrate | 0.012 | L-lactate | 1.000 | 0.45 | 4.09 |
| CEM-101 | 2 | Tartrate | 0.023 | L-lactate | 1.000 | 0.45 | 4.09 |
| CEM-101 | 3 | Tartrate | 0.035 | L-lactate | 1.000 | 0.45 | 3.94 |

In each case, the addition of lactic acid decreases the observed amount of precipitation to BQL. The addition of lactic acid also decreases the amount of precipitation observed in the samples that include citrate. Azithromycin infused as a citrate buffered solution in 0.45% saline at 2 mg/mL and 4 mL/min, does not exhibit precipitation (BQL). Comparison of 3 mg/mL CEM-101 lyo in 5 mM citrate buffer at pH 4 with 3 mg/mL CEM-101 lyo in 0.45% saline at infusion rates of 1 mL/min, 2 mL/min and 3 mL/min shows precipitation from both solutions at all infusion rates, but precipitation at 1 mL/min is reduced in the 5 mM citrate buffer solution, where at 1 mL/min an absorbance of <0.05 was observed, where as at 2 or 3 mL/min, an absorbance of >0.05 was observed. The use of a citrate buffer diluent did not dramatically reduce precipitation in the absence of lactate.

Variation of Lactate Forms and Buffer Concentrations

Example

Lactic acid based formulations in 0.45% saline vehicle. The following are prepared using CEM-101 lyo (which includes the 0.012% tartrate per gram of CEM-101 and any additional tartrate necessary for the concentration indicated as Buffer 1) and the indicated lactate buffer.

| Compound | (mg/mL) Drug | % Tartrate | Lactate | % | % Saline | pH |
|---|---|---|---|---|---|---|
| CEM-101 | 2 | 0.023 | | | 0.50 | |
| CEM-101 | 2 | 0.023 | L-Lactate | 0.500 | 0.50 | 4.06 |
| CEM-101 | 2 | 0.023 | DL-Lactate | 0.500 | 0.50 | 3.91 |
| CEM-101 | 2 | 0.075 | L-Lactate | 0.500 | 0.50 | 3.95 |
| CEM-101 | 2 | 0.150 | L-Lactate | 0.500 | 0.50 | 3.98 |
| CEM-101 | 2 | 0.023 | L-Lactate | 0.250 | 0.50 | 4.09 |
| CEM-101 | 2 | 0.075 | L-Lactate | 0.250 | 0.50 | 4.02 |
| CEM-101 | 2 | 0.150 | L-Lactate | 0.250 | 0.50 | 3.96 |
| CEM-101 | 2 | 0.375 | L-Lactate | 0.250 | 0.50 | 4.04 |
| CEM-101 | 2 | 0.023 | L-Lactate | 0.500 | 0.50 | 4.00 |
| CEM-101 | 2 | 0.023 | DL-Lactate | 0.500 | 0.50 | 4.00 |

| Compound | (mg/mL) Drug | % Tartrate | % L-Lactate | % Citrate | % Saline | pH |
|---|---|---|---|---|---|---|
| Placebo | 0 | | | | 0.45 | |
| CEM-101 | 2 | 0.023 | | | 0.50 | |
| CEM-101 | 3 | 0.035 | | | 0.50 | |
| CEM-101 | 2 | 0.023 | 0.500 | | 0.50 | 4.04 |
| CEM-101 | 2 | 0.150 | 1.000 | | 0.50 | 3.94 |
| CEM-101 | 3 | 0.150 | 1.000 | | 0.50 | 3.93 |
| CEM-101 | 2 | 0.375 | 1.000 | | 0.50 | 3.96 |

-continued

| Compound | (mg/mL) Drug | % Tartrate | % L-Lactate | % Citrate | % Saline | pH |
|---|---|---|---|---|---|---|
| CEM-101 | 3 | 0.375 | 1.000 |  | 0.50 | 3.97 |
| CEM-101 | 2 | 0.023 | 1.000 | 0.009 | 0.50 | 4.00 |
| CEM-101 | 3 | 0.035 | 1.000 | 0.009 | 0.50 | 4.02 |
| CEM-101 | 2 | 0.023 | 1.000 | 0.019 | 0.50 | 3.98 |
| CEM-101 | 3 | 0.035 | 1.000 | 0.019 | 0.50 | 3.97 |
| CEM-101 | 2 | 0.023 | 1.000 | 0.096 | 0.50 | 3.90 |
| CEM-101 | 3 | 0.035 | 1.000 | 0.096 | 0.50 | 3.92 |

Evaluation of 2 mg/mL and 1 mg/mL CEM-101 lyo-based Formulation (CEM-101) in 0.5% lactate buffer at pH 4 in 0.5% saline at infusion rates of 1 mL/min, 2 mL/min and 3 mL/min shows precipitation below the threshold absorbance level of 0.003 at each of the three rates (showing comparison with 2 mg/mL CEM-101 lyo-based Formulation (CEM-101) in 0.45% saline). All lactate containing formulations showed an absorbance <0.01. All non-lactate containing gave showed an absorbance of about 0.03 in at least one infusion/concentration combination.

Infusions of 2 mg/mL CEM-101 lyo in 1% lactate formulation at pH 4 in 0.5% saline with a variety of vehicles at infusion rates of 1 mL/min, 2 mL/min and 3 mL/min generally show precipitation below the threshold absorbance level of 0.003 at each of the three rates. Similar infusions of 3 mg/mL CEM-101 lyo-based Formulation show precipitation greatly reduced compared to the formulation without 1% lactate buffer or show precipitation below the threshold absorbance level of 0.003. Overall, the use of 1.0% and 0.5% L-lactate produces a greater reduction of precipitation than 0.25% L-lactate.

Infusions of solutions using DL-lactic acid buffer gives results comparable to those of solutions using L-lactic acid buffers and shows infusions at infusion rates of 1 mL/min, 2 mL/min and 3 mL/min of 2 mg/mL CEM-101 lyo-based Formulation (CEM-101) in 0.5% saline, 0.5% L-lactate buffer at pH 4 in 0.5% saline, 0.5% DL-lactate buffer at pH 4 in 0.5% saline, and 0.5% L-lactate buffer plus 5 mM tartaric acid buffer at pH 4 in 0.5% saline).

The use of additional tartrate buffer did not dramatically reduce precipitation. The use of either L-lactate buffer or DL-lactate buffer reduced precipitation in all cases.

In summary, 0.5, 1 and 5 mM citrate buffer (pH 4) in 0.45% saline does not significantly reduce precipitation in the dynamic precipitation model at concentrations of 2 mg/mL and 3 mg/mL SOL formulations. 10 or 25 mM tartrate buffer (pH 4) in 0.45% saline does not significantly reduce precipitation in the dynamic precipitation model at concentrations of 2 mg/mL and 3 mg/mL SOL formulations. In both 0.5% and 1% lactate buffer (pH 4) in 0.45% saline precipitation is reduced below the 0.003 absorbance level at 1 mg/mL and 2 mg/mL at a rate of 3 mL/min. Addition of a citrate or tartrate co-buffer to the lactate buffer had minimal effect in the dynamic precipitation model.

Example

Amino Acid Formulations. The following illustrative formulations are prepared using SOL. It is understood that any source of SOL may be used as described herein. The illustrative formulations are tested in the Dynamic Precipitation Model and show an absorbance of less than about 0.01.

| Formulation Agents | pH | SOL Concentration | Infusion Rate |
|---|---|---|---|
| 25 mM Histidine + 25 mM Glutamic Acid + 25 mM Acetic Acid | n/a | 0 mg/ml | 3 ml/min |
| 25 mM Histidine + 25 mM Glutamic Acid + 15 mM Acetic Acid | n/a | 0 mg/ml | 3 ml/min |
| 25 mM Histidine + 25 mM Glutamic Acid + 25 mM Aspartic Acid | n/a | 0 mg/ml | 3 ml/min |
| 25 mM Histidine + 25 mM Glutamic Acid | 5.0 | 2 mg/ml | 3 ml/min |
| 20 mM Histidine + 25 mM Glutamic Acid | 5.0 | 2 mg/ml | 3 ml/min |
| 20 mM Histidine + 20 mM Glutamic Acid | 5.0 | 2 mg/ml | 3 ml/min |
| 20 mM Histidine + 20 mM Glutamic Acid + 20 mM Tartaric Acid | 5.0 | 2 mg/ml | 3 ml/min |
| 20 mM Histidine + 20 mM Glutamic Acid + 20 mM Acetic Acid | 5.0 | 2 mg/ml | 3 ml/min |
| 25 mM Histidine + 25 mM Glutamic Acid + 25 mM Acetic Acid | 5.0 | 2 mg/ml | 3 ml/min |
| 25 mM Histidine + 25 mM Glutamic Acid + 25 mM Acetic Acid | 5.0 | 2 mg/ml | 3 ml/min |
| 15 mM Histidine + 15 mM Glutamic Acid + 15 mM Acetic Acid | 5.0 | 2 mg/ml | 3 ml/min |
| 15 mM Histidine + 15 mM Glutamic Acid + 15 mM Acetic Acid | 5.0 | 2 mg/ml | 3 ml/min |
| 10 mM Histidine + 10 mM Glutamic Acid + 10 mM Acetic Acid | 5.0 | 2 mg/ml | 3 ml/min |
| 25 mM Histidine + 25 mM Glutamic Acid + 15 mM Acetic Acid | 5.0 | 2 mg/ml | 3 ml/min |
| 15 mM Histidine + 15 mM Glutamic Acid + 15 mM Acetic Acid* | 5.0 | 2 mg/ml | 3 ml/min |

| Formulation Agents | pH | SOL Concentration | Infusion Rate |
|---|---|---|---|
| 25 mM Histidine + 25 mM Acetic Acid | 5.0 | 2 mg/ml | 3 ml/min |
| 25 mM Histidine + 25 mM Acetate | 6.0 | 2 mg/mL | 3 mL/min |
| 15 mM Histidine + 15 mM Glutamic Acid + 15 mM Acetic Acid | 4.5 | 2 mg/ml | 3 ml/min |
| 15 mM Histidine + 15 mM Glutamic Acid + 15 mM Acetic Acid | 4.2 | 2 mg/ml | 3 ml/min |
| 15 mM Histidine + 15 mM Glutamic Acid + 15 mM Aspartic Acid | 4.5 | 2 mg/ml | 3 ml/min |
| 15 mM Histidine + 15 mM Glutamic Acid + 15 mM Aspartic Acid | 4.5 | 2 mg/ml | 3 ml/min |
| 15 mM Histidine + 15 mM Glutamic Acid + 15 mM Lactic Acid | 4.5 | 2 mg/ml | 3 ml/min |
| 15 mM Histidine + 15 mM Glutamic Acid + 15 mM Aspartic Acid | 4.2 | 2 mg/ml | 3 ml/min |
| 15 mM Histidine + 15 mM Glutamic Acid + 15 mM Lactic Acid | 4.2 | 2 mg/ml | 3 ml/min |
| 25 mM Histidine + 25 mM Glutamic Acid + 25 mM Aspartic Acid | 4.0 | 2 mg/ml | 3 ml/min |
| 15 mM Histidine + 15 mM Glutamic Acid | 5.0 | 2 mg/ml | 3 ml/min |
| 25 mM Histidine + 25 mM Lactic Acid + | 6.0 | 2 mg/mL | 3 mL/min |
| 25 mM Histidine + 25 mM Acetic Acid + | 6.0 | 2 mg/mL | 3 mL/min |
| 25 mM Histidine + 25 mM Lactate + 25 mM Acetate | 6.0 | 2mg/mL | 3 mL/min |
| 25 mM Histidine | 6.0 | 2 mg/mL | 3 mL/min |
| 25 mM Histidine | 5.5 | 2 mg/mL | 3 mL/min |
| 25 mM Histidine + 25 mM Phosphate | 5.5 | 2 mg/mL | 3 mL/min |
| 25 mM Histidine + 10 mM Phosphate | 5.5 | 2 mg/mL | 3 mL/min |
| 5 mM Glutamic Acid + 5 mM Histidine + 5 mM Acetic Acid + 5% Mannitol | 5.5 | 2 mg/mL | 3 mL/min |
| 5 mM Glutamic Acid + 5 mM Histidine + 5% Mannitol | 5.5 | 2 mg/mL | 3 mL/min |
| 5 mM Glutamic Acid + 10 mM Histidine + 5% Mannitol | 5.5 | 2 mg/mL | 3 mL/min |
| 5 mM Glutamic Acid + 15 mM Histidine + 5% Mannitol | 5.5 | 2 mg/mL | 3 mL/min |
| 15 mM Histidine + 5% Mannitol | 5.5 | 2 mg/mL | 3 mL/min |
| 10 mM Histidine + 0.5% Poloxamer-188 + 5% Mannitol | 6.0 | 2 mg/mL | 3 mL/min |
| 15 mM Histidine + 0.5% Poloxamer-188 + 5% Mannitol | 6.0 | 2 mg/mL | 3 mL/min |
| 10 mM Histidine + 1.0% Captisol + 5% Mannitol | 6.0 | 2 mg/mL | 3 mL/min |
| 10 mM Histidine + 2.0% Captisol + 5% Mannitol | 6.0 | 2 mg/mL | 3 mL/min |
| 15 mM Histidine + 15 mM Glutamic Acid + 15 mM Aspartic Acid + 4.3% Mannitol | 5.4 | 2 mg/mL | 10 mL/min |
| 15 mM Histidine + 15 mM Glutamic Acid + 15 mM Aspartic Acid + 4.3% Mannitol | 5.4 | 2 mg/mL | 5 mL/min |
| 25 mM Histidine + 15 mM Glutamic Acid + 4.6% Mannitol | 5.5 | 2 mg/mL | 10 mL/min |
| 15 mM Histidine + 25 mM Lactic Acid + 4.3% Mannitol | 6.0 | 2 mg/mL | 10 mL/min |
| 25 mM Histidine + 25 mM Lactic Acid + 25 mM Acetic Acid + 3.4% Mannitol | 6.1 | 2 mg/mL | 10 mL/min |
| 25 mM Histidine + 15 mM Glutamic Acid + 4.7% Mannitol | 6.1 | 2 mg/mL | 10 mL/min |
| 15 mM Histidine + 25 mM Lactic Acid + 4.3% Mannitol | 6.5 | 2 mg/mL | 10 mL/min |
| 25 mM Histidine + 25 mM Lactic Acid + 25 mM Acetic Acid + 3.2% Mannitol | 6.6 | 2 mg/mL | 10 mL/min |
| 25 mM Histidine + 15 mM Glutamic Acid + 4.6% Mannitol | 6.5 | 2 mg/mL | 10 mL/min |
| 15 mM Histidine + 15 mM Glutamic Acid + 4.7% Mannitol | 6.4 | 2 mg/mL | 10 mL/min |
| 15 mM Histidine + 15 mM Acetic Acid + 15 mM Lactic Acid + 4.4% Mannitol | 5.4 | 2 mg/mL | 10 mL/min |
| 15 mM Histidine + 15 mM Acetic Acid + 15 mM Lactic Acid + 4.4% Mannitol | 5.8 | 2 mg/mL | 10 mL/min |
| 15 mM Histidine + 15 mM Acetic Acid + 15 mM Lactic Acid + 0.9% NaCl | 5.5 | 2 mg/mL | 10 mL/min |
| 15 mM Histidine + 15 mM Glutamic Acid + 15 mM Aspartic Acid + 0.9% NaCl | 5.4 | 2 mg/mL | 10 mL/min |
| 15 mM Histidine + 15 mM Acetic Acid + 15 mM Lactic Acid + 0.45% NaCl | 5.5 | 2 mg/mL | 10 mL/min |
| 15 mM Histidine + 15 mM Glutamic Acid + 15 mM Aspartic Acid + 0.45% NaCl | 5.6 | 2 mg/mL | 10 mL/min |
| 15 mM Histidine + 15 mM Glutamic Acid + 15 mM Acetic Acid + 4.3% Mannitol | 5.0 | 2 mg/mL | 10 mL/min |
| 15 mM Histidine + 15 mM Glutamic Acid + 15 mM Aspartic Acid + 5% Mannitol | 4.5 | 2 mg/mL | 10 mL/min |
| 15 mM Histidine + 15 mM Glutamic Acid + 15 mM Aspartic Acid + 2% Mannitol + 0.45% NaCl | 4.5 | 4 mg/mL | 10 mL/min |

-continued

| Formulation Agents | pH | SOL Concentration | Infusion Rate |
|---|---|---|---|
| 15 mM Histidine + 15 mM Glutamic Acid + 15 mM Aspartic Acid + 2% Mannitol + 0.45% NaCl | 4.5 | 4 mg/mL | 5 mL/min |
| 15 mM Histidine + 15 mM Glutamic Acid + 15 mM Aspartic Acid + 0.9% NaCl | 4.5 | 4 mg/mL | 10 mL/min |
| 15 mM Histidine + 15 mM Glutamic Acid + 15 mM Aspartic Acid + 0.9% NaCl | 4.5 | 4 mg/mL | 5 mL/min |

Method Example

Pain Tolerance Evaluation Following Intravenous Infusion in Rabbit. Single Dose Rabbit Ear Vein Model Study. New Zealand White female rabbits weighing 2.5-3.2 kg are evaluated for pain, ear inflammation and phlebitis after intravenous infusion of test compound. Commercial azithromycin citrate is used as a positive control.

CEM-101 lyo (SOL (250.0 mg), mannitol, USP (250.0 mg), L(+)-tartaric acid, USP (29.0 mg), sodium hydroxide, NF (for pH adjustment to pH 4.2)) is reconstituted in a vehicle or formulation as described herein. The placebo is the same formulation without SOL. The reconstituted SOL or placebo is dissolved in an appropriate vehicles, such as 0.45% saline, 0.5% lactic acid at pH 4 in 0.45% saline, 0.5% lactic acid with 10 mM tartaric acid at pH 4 in 0.45% saline. CEM-101 lyo is dissolved in the appropriate vehicle at concentrations of 2 mg/mL or 3 mg/mL. The CEM-101 placebo formulation is dissolved in 0.45% saline. All rabbits are weighed to calculate dosing volumes.

Azithromycin lyophilized vials are commercially available azithromycin citrate for injection (ZITHROMAX IV) in lyophilized form in a 10-mL vial equivalent to 500 mg of azithromycin for intravenous administration. Reconstitution, according to label directions, results in approximately 5 mL of ZITHROMAX for intravenous injection with each mL containing azithromycin dihydrate equivalent to 100 mg of azithromycin. Reconstituted azithromycin Citrate, 2 mg/mL, is dissolved in its vehicle, 0.45% saline.

Two rabbits are dosed with vehicle then with azithromycin citrate via intravenous infusion in a marginal ear vein at a dose volume of 5 mL and an infusion rate of 4 mL/min. Two rabbits are dosed with vehicle (4 mL/min) then with test compound in a formulation described herein or a comparative formulation saline via intravenous infusion in a marginal ear vein at a dose volume of 5 mL and/or concentration of 2 mg/mL and/or 3 mg/mL at infusion rates of 1, 2, 3, and/or 4 mL/min. After evaluation, the study continued with dosing of CEM-101/Mannitol/Tartrate Formulation in the lactate containing vehicles. All rabbits received vehicle, 0.5 N saline (azithromycin citrate) or CEM-101 placebo formulation in 0.45% saline (CEM-101 dosed animals) in the left ear and test article in the right ear. Thirty minutes was allowed to lapse between each infusion in the same animal.

Animals were observed during and post (30 minutes) each infusion, and reactions were scored according to a modified Draize Score and recorded. The Modified Draize Score used to evaluate the rabbits' reactions to test article administration was as follows:

0—No Reaction
1—slight twitch of the ear when IV infusion administered
2—ear twitch and head movement
3—strong head movement on administration but quiets in 20 seconds
4—strong movement of ear, head, and body with vocalization Rabbits receiving SOL in 0.45% saline experienced adverse effects from a slight twitch of the ear upon test article administration to strong head movement on administration, though becoming calm in approximately 20 seconds. The severity of the reactions correlated with the increasing infusion rate. Rabbits receiving SOL in any of the lactate formulations displayed no reactions upon test article administration during any of the infusions at either concentration (2 mg/mL or 3 mg/mL); and pain, inflammation and phlebitis were not observed.

Rabbits receiving Azithromycin Citrate experienced strong movement of ear, head and body with vocalization upon test article administration and were removed from the study.

Modified Draize Scores for Tested Formulations

| Example | Vehicle | 1 mL/min | 2 mL/min | 3 mL/min | 4 mL/min |
|---|---|---|---|---|---|
| SOL in 0.45% saline (2 mg/mL) | 1 | 1 | 1 | 2 | 3 |
| SOL in 0.5% lactic acid at pH 4 in 0.45% saline (2 mg/mL) | 0 | 0 | 0 | 0 | 0 |
| SOL in 0.5% lactic acid at pH 4 in 0.45% saline (3 mg/mL) | 0 | 0 | 0 | 0 | 0 |
| SOL in 0.5% lactic acid with 10 mM tartaric acid at pH 4 in 0.45% saline (2 mg/mL) | 0 | 0 | 0 | 0 | 0 |
| SOL in 0.5% lactic acid with 10 mM tartaric acid at pH 4 in 0.45% saline (3 mg/mL) | 0 | 0 | 0 | 0 | 0 |
| Azithromycin Citrate in 0.45% saline (2 mg/mL) | 0 | — | — | — | 4 |

Method Example

Tolerance Evaluation of Following Intravenous Infusion in the Rabbit. Multiple-Dose Rabbit Ear Vein Model Study. New Zealand White female rabbits weighing 2.5-3.2 kg are evaluated for pain, ear inflammation and phlebitis after receiving an intravenous infusion of test compound once daily for 5 days.

SOL is dissolved in a 0.5% lactic acid formulation at pH 4, and then into 0.45% saline at concentrations of 2 mg/mL or 3 mg/mL.

Four rabbits are dosed; one vehicle-dosed and one each at 2 mg/mL (rate of 3 mL/min), 3 mg/mL (rate of 3 mL/min) and 3 mg/mL (rate of 4 mL/min). All rabbits receive a dose volume of 5 mL and are dosed via intravenous infusion in the right marginal ear vein once daily for 5 days. Animals are observed during and post (30 minutes) each infusion and reactions recorded.

No adverse effects were observed in any of the rabbits on Days 1 and 2. On Days 4 and 5, mechanical irritation around the needle stick, without reaction distal to the needle, was seen in the vehicle-treated and 2 mg/mL (rate of 3 mL/min) rabbits. Rabbits receiving SOL at a concentration of 3 mg/mL and rates of 3 or 4 mL/min experienced vessel dilation and irritation around and past the needle stick beginning on Day 3 and continuing until day 5. Head and ear twitching was also observed in the rabbit receiving 3 mg/mL of SOL at a rate of 4 mL/min.

Method Example

Dermal Erythema, Edema, and Phlebitis model. Test compounds are compared to the corresponding vehicle controls. The test and vehicle control formulations are prepared fresh on the day of dosing and used within 4 hours of preparation. The control 0.9% NaCl for Injection, USP is used as supplied. The vehicle controls are prepared five days prior to the start of dosing in a quantity sufficient enough for a treatment period of up to 5 days. All formulations are prepared using Sterile Water for Injection USP. Twenty-six (26) male New Zealand White rabbits (*Oryctolagus cuniculus*) are used in this Example. Rabbits are generally 3 to 4 months old and their body weights range from 2.3 to 3.6 kg. Test compounds are administered as a single dose over a period of 2 or 20 minutes (total volume of 10 mL) by intravenous infusion to New Zealand White rabbits (n=3). Test compounds are injected into the marginal ear veins (right ear) via disposable indwelling catheters. Corresponding vehicle controls are injected into the marginal ear veins (left ear) via disposable indwelling catheters. A positive control group is tested with 0.9% NaCl for Injection, USP in each ear. All test animals are evaluated for ear dermal erythema and/or edema. Infusion rates are fixed and independent of animal weight. Final dose level in mg/kg is dependent on the individual animal's body weight.

Following dosing, all animals were observed for approximately 24 hours and then euthanized and subjected to an external examination followed by collection of tissues for histopathological examinations. Parameters monitored include mortality, clinical observations, body weight, dermal changes (using a modified Draize scoring scheme) and macroscopic and microscopic (histopathological) examination of the ear (dosing site) and jugular veins. Only one rabbit in Group 3 (15 mM L-(−)-Histidine, 15 mM L-(+)-Glutamic Acid, 15 mM L-(+)-Aspartic acid in 0.9% Saline vehicle at pH 4.5) developed a well-defined erythema at 23 hour after the dosing. Ear edema was not observed in any groups under either infusion condition. No Macroscopic findings at necropsy were observed in any of the treatment groups. The histopathological findings at 1 cm and most distal location (junction of the ear and head) at approximately 2 cm from the catheter tips were minimal or mild in all the groups. No findings were observed at the jugular vein site in any groups dosed at 5 mL/min or 0.5 mL/min.

What is claimed is:
1. A pharmaceutical composition adapted for intravenous administration, the composition comprising one or more antibiotic compounds and a formulating agent, wherein the formulating agent comprises an amino acid selected from the group consisting of arginine, asparagine, aspartic acid, cysteine, glutamine, glutamic acid, histidine, lysine, ornithine, serine, threonine, tryptophan, and tyrosine, and pharmaceutically acceptable salts thereof, and combinations thereof; and where at least one of the one or more antibiotic compounds is of the formula

| Formulation | Vehicle | Dose (mg) | Concentration (mg/mL) | Infusion Rate (mL/min) | Infusion Length (min) |
|---|---|---|---|---|---|
| 15 mM L-(−)-Histidine 15 mM L-(+)-Glutamic Acid 15 mM L-(+)-Aspartic acid | 4.3% D-(+)-Mannitol at pH 4.5 | 25 | 2.5 | 5 | 2 |
| 15 mM L-(−)-Histidine 15 mM L-(+)-Glutamic Acid 15 mM L-(+)-Aspartic acid | 0.9% Saline at pH 4.5 | 25 | 2.5 | 5 | 2 |
| 38.5 mM L-(−)-Tartaric acid 0.5% Monothioglycerol (1-thioglycerol) | 3% D-(+)-Mannitol at pH 4.2 | 25 | 2.5 | 5 | 2 |
| 15 mM L-(−)-Histidine 15 mM L-(+)-Glutamic Acid 15 mM L-(+)-Aspartic acid | 4.3% D-(+)-Mannitol at pH 4.5 | 25 | 2.5 | 0.5 | 20 |
| 15 mM L-(−)-Histidine 15 mM L-(+)-Glutamic Acid 15 mM L-(+)-Aspartic acid | 0.9% Saline at pH 4.5 | 25 | 2.5 | 0.5 | 20 |
| 38.5 mM L-(−)-Tartaric acid 0.5% Monothioglycerol (1-thioglycerol) | 3% D-(+)-Mannitol at pH 4.2 | 25 | 2.5 | 0.5 | 20 |
| 15 mM L-(−)-Histidine 15 mM L-(+)-Glutamic Acid 15 mM Acetic Acid (from Sodium acetate trihydrate) | 4.1% Mannitol at pH 5.0 | 25 | 2.5 | 0.5 | 20 |

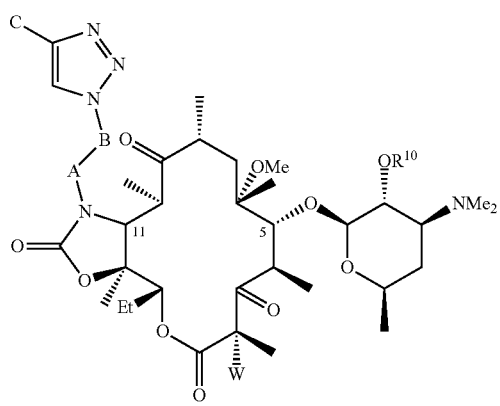

or a pharmaceutically acceptable salt thereof, wherein:
$R^{10}$ is hydrogen, acyl or a prodrug moiety;
W is H, F, Cl, Br, I, or OH;
A is $CH_2$, C(O), C(O)O, C(O)NH, $S(O)_2$, $S(O)_2NH$, or $C(O)NHS(O)_2$;
B is $C_2$-$C_{10}$ alkenylene or $C_1$-$C_{10}$ alkylene; and
C is hydrogen, hydroxy, acyl, acyloxy, sulfonyl, ureido, or carbamoyl, or alkyl, alkoxy, heteroalkyl, heteroalkoxy, aryl, arylalkyl, heteroaryl, or heteroarylalkyl, each of which is optionally substituted.

2. The composition of claim 1 wherein $R^{10}$ is hydrogen.
3. The composition of claim 1 wherein W is H or F.
4. The composition of claim 1 wherein W is F.
5. The composition of claim 1 wherein A is $CH_2$.
6. The composition of claim 1 wherein B is $C_1$-$C_{10}$ alkylene.
7. The composition of claim 1 wherein B is $(CH_2)_n$, where n is an integer from 1 to 10.
8. The composition of claim 1 wherein B is $(CH_2)_3$.
9. The composition of claim 1 wherein C is optionally substituted aryl.
10. The composition of claim 1 wherein one of the antibiotic compounds is solithromycin, or a pharmaceutically acceptable salt thereof.
11. The composition of claim 1 wherein the amino acid is selected from the naturally occurring amino acids having the natural L configuration, and pharmaceutically acceptable salts thereof, and combinations thereof.
12. The composition of claim 1 wherein the amino acid is selected from the group consisting of histidine, aspartic acid, glutamic acid, and pharmaceutically acceptable salts of the foregoing, and any combination thereof.
13. The composition of claim 1 wherein the amino acid is histidine or a pharmaceutically acceptable salt thereof, aspartic acid or a pharmaceutically acceptable salt thereof, and glutamic acid or a pharmaceutically acceptable salt thereof, or a combination thereof.
14. The composition of claim 1 further comprising a liquid vehicle.
15. The composition of claim 14 wherein the liquid vehicle contains about 0.9% by weight sodium chloride or less.
16. The composition of claim 14 wherein the liquid vehicle contains about 0.45% by weight sodium chloride or less.
17. The composition of claim 14 wherein the liquid vehicle is substantially free of sodium chloride.
18. The composition of claim 14 wherein the formulation has a pH in the range from about 3.5 to about 6.
19. A kit comprising a composition of claim 1, and instructions for the preparation of a pharmaceutically acceptable infusion solution thereof.
20. A method for treating a host animal having a bacterial infection, the method comprising the step of administering by intravenous injection to the host animal a therapeutically effective amount of a composition of claim 14.
21. The composition of claim 10 wherein the amino acid is selected from the naturally occurring amino acids having the L configuration, and pharmaceutically acceptable salts thereof, and combinations thereof.
22. The composition of claim 10 wherein the amino acid is selected from the group consisting of histidine, aspartic acid, glutamic acid, and pharmaceutically acceptable salts of the foregoing, and any combination thereof.
23. The composition of claim 10 wherein the amino acid is histidine or a pharmaceutically acceptable salt thereof, aspartic acid or a pharmaceutically acceptable salt thereof, and glutamic acid or a pharmaceutically acceptable salt thereof, or a combination thereof.
24. The composition of claim 10 further comprising a liquid vehicle that contains about 0.9% by weight sodium chloride or less.
25. The composition of claim 24 wherein the liquid vehicle contains about 0.45% by weight sodium chloride or less.
26. The composition of claim 24 wherein the liquid vehicle is substantially free of sodium chloride.
27. A kit comprising the composition of claim 10, and instructions for the preparation of a pharmaceutically acceptable infusion solution thereof.
28. A method for treating a host animal having a bacterial infection, the method comprising administering to the host animal a therapeutically effective amount of a composition of claim 24 by intravenous injection.

* * * * *